United States Patent
Loew et al.

(10) Patent No.: US 10,253,313 B2
(45) Date of Patent: Apr. 9, 2019

(54) UNIVERSAL FIBRONECTIN TYPE III BOTTOM-SIDE BINDING DOMAIN LIBRARIES

(71) Applicants: Andreas Loew, Cambridge, MA (US); Brian Vash, Cambridge, MA (US)

(72) Inventors: Andreas Loew, Cambridge, MA (US); Brian Vash, Cambridge, MA (US)

(73) Assignee: Novartis AG, Basel (CH)

( * ) Notice: Subject to any disclaimer, the term of this patent is extended or adjusted under 35 U.S.C. 154(b) by 202 days.

(21) Appl. No.: 14/828,763

(22) Filed: Aug. 18, 2015

(65) Prior Publication Data

US 2016/0194626 A1    Jul. 7, 2016

Related U.S. Application Data

(63) Continuation of application No. 13/504,824, filed as application No. PCT/EP2010/066250 on Oct. 27, 2010, now Pat. No. 9,139,825.

(60) Provisional application No. 61/256,409, filed on Oct. 30, 2009.

(51) Int. Cl.
| C40B 40/10 | (2006.01) |
| C12N 15/10 | (2006.01) |
| C40B 30/02 | (2006.01) |
| C40B 50/02 | (2006.01) |
(Continued)

(52) U.S. Cl.
CPC ..... *C12N 15/1037* (2013.01); *C12N 15/1044* (2013.01); *C40B 30/02* (2013.01); *C40B 50/02* (2013.01); *G01N 33/566* (2013.01); *G06F 19/16* (2013.01); *C40B 40/10* (2013.01)

(58) Field of Classification Search
None
See application file for complete search history.

(56) References Cited

U.S. PATENT DOCUMENTS

| 4,725,677 A | 2/1988 | Koster et al. |
| 4,888,286 A | 12/1989 | Crea |
| 5,324,637 A | 6/1994 | Thompson et al. |
(Continued)

FOREIGN PATENT DOCUMENTS

| AU | 2003243436 | 12/2003 |
| AU | 2004283299 | 6/2009 |
(Continued)

OTHER PUBLICATIONS

McCarthy et al. (May 1, 2001) Journal of Immunological Methods vol. 251 pp. 137 to 149.*
(Continued)

*Primary Examiner* — Christian C Boesen
(74) *Attorney, Agent, or Firm* — Linyu L. Mitra

(57) ABSTRACT

The invention pertains to a natural-variant combinatorial library of fibronectin Type 3 domain (Fn3) polypeptides useful in screening for the presence of one or more polypeptides having a selected binding or enzymatic activity. The library polypeptides include (a) regions A, AB, B, C, CD, D, E, EF, F, and G having wildtype amino acid sequences of a selected native fibronectin Type 3 polypeptide or polypeptides, and (b) loop regions AB, CD, and EF having selected lengths (Bottom Loops). The Fn3 may also have loop regions BC, DE, and FG having wildtype amino acid sequences, having selected lengths, or mutagenized amino acid sequences (Top Loops).

12 Claims, 18 Drawing Sheets

Specification includes a Sequence Listing.

AB Loop
*Loop length distribution*
AB LOOP

(51) Int. Cl.
*G06F 19/16* (2011.01)
*G01N 33/566* (2006.01)

(56) References Cited

U.S. PATENT DOCUMENTS

| | | |
|---|---|---|
| 5,492,817 A | 2/1996 | Thompson et al. |
| 5,629,204 A | 5/1997 | Honjo et al. |
| 5,665,563 A | 9/1997 | Beckler |
| 5,695,941 A | 12/1997 | Brent et al. |
| 5,698,520 A | 12/1997 | Honjo et al. |
| 5,798,208 A | 8/1998 | Crea |
| 5,830,650 A | 11/1998 | Crea |
| 6,132,963 A | 10/2000 | Brent et al. |
| 6,214,553 B1 | 4/2001 | Szostak et al. |
| 6,258,558 B1 | 7/2001 | Szostak et al. |
| 6,261,804 B1 | 7/2001 | Szostak et al. |
| 6,300,065 B1 | 10/2001 | Kieke et al. |
| 6,348,315 B1 | 2/2002 | Pluckthum et al. |
| 6,423,538 B1 | 7/2002 | Wittrup et al. |
| 6,462,189 B1 | 10/2002 | Koide |
| 6,649,340 B1 | 11/2003 | Crea |
| 6,673,901 B2 | 1/2004 | Koide |
| 6,703,199 B1 | 3/2004 | Koide |
| 6,818,418 B1 | 11/2004 | Lipovek et al. |
| 6,841,352 B2 | 1/2005 | Ostanin |
| 7,078,490 B2 | 7/2006 | Koide |
| 7,115,396 B2 | 10/2006 | Lipovek et al. |
| 7,119,171 B2 | 10/2006 | Koide |
| 7,153,661 B2 | 12/2006 | Koide |
| 7,598,352 B2 | 10/2009 | Koide |
| 7,847,062 B2 | 12/2010 | Chen et al. |
| 7,858,090 B2 | 12/2010 | Koide |
| 7,981,620 B2 | 7/2011 | Koide |
| 8,062,858 B2 | 11/2011 | Koide |
| 8,106,162 B2 | 1/2012 | Koide |
| 8,258,265 B2 | 9/2012 | Koide |
| 8,263,741 B2 | 9/2012 | Koide |
| 2002/0019517 A1 | 2/2002 | Koilde |
| 2003/0003439 A1 | 1/2003 | Ostanin |
| 2003/0027319 A1 | 2/2003 | Koide |
| 2003/0036092 A1 | 2/2003 | Iverson et al. |
| 2003/0100023 A1 | 5/2003 | Iverson et al. |
| 2003/0157132 A1 | 8/2003 | Itami et al. |
| 2003/0186385 A1 | 10/2003 | Koide |
| 2004/0058403 A1 | 3/2004 | Harvey et al. |
| 2004/0072740 A1 | 4/2004 | Iverson et al. |
| 2005/0038229 A1 | 2/2005 | Lipovsek et al. |
| 2005/0136428 A1 | 6/2005 | Crea |
| 2005/0255548 A1 | 11/2005 | Lipovsek et al. |
| 2006/0233854 A1 | 10/2006 | Seliktar et al. |
| 2006/0233855 A1 | 10/2006 | Seliktar et al. |
| 2006/0240018 A1 | 10/2006 | Koide et al. |
| 2006/0246059 A1 | 11/2006 | Lipovsek et al. |
| 2006/0270045 A1 | 11/2006 | Cregg et al. |
| 2006/0270604 A1 | 11/2006 | Lipovsek et al. |
| 2007/0082365 A1 | 4/2007 | Lipovsek et al. |
| 2007/0148126 A1 | 6/2007 | Chen et al. |
| 2008/0003643 A1 | 1/2008 | Cregg et al. |
| 2008/0015339 A1 | 1/2008 | Lipovsek et al. |
| 2008/0063651 A1 | 3/2008 | Lipovsek et al. |
| 2008/0108798 A1 | 5/2008 | Lipovsek et al. |
| 2008/0139791 A1 | 6/2008 | Lipovsek et al. |
| 2009/0176654 A1 | 7/2009 | Cappuccilli et al. |
| 2009/0253899 A1 | 10/2009 | Koide |
| 2009/0299040 A1 | 12/2009 | Camphausen et al. |
| 2010/0278801 A1 | 11/2010 | Shepard et al. |
| 2010/0322930 A1 | 12/2010 | Kolbinger et al. |
| 2011/0038866 A1 | 2/2011 | Hastewell et al. |
| 2011/0229406 A1 | 9/2011 | Hettmann et al. |
| 2012/0135516 A1 | 5/2012 | Koide |
| 2012/0208704 A1 | 8/2012 | Loew et al. |

FOREIGN PATENT DOCUMENTS

| | | |
|---|---|---|
| AU | 2009213095 | 10/2009 |
| CA | 2541651 | 5/2005 |
| CN | 1871359 | 11/2006 |
| EP | 670369 | 9/1995 |
| EP | 1137941 | 10/2001 |
| EP | 1266025 | 12/2002 |
| EP | 1356075 | 10/2003 |
| EP | 1678314 | 7/2006 |
| EP | 1722834 | 11/2006 |
| JP | 2002532072 | 10/2002 |
| JP | 2003525487 | 8/2003 |
| JP | 2004526419 | 9/2004 |
| JP | 2007508847 | 4/2007 |
| KR | 100778219 | 11/2007 |
| NO | 20062134 | 6/2006 |
| NZ | 547279 | 4/2008 |
| WO | WO 1998/056915 | 12/1998 |
| WO | WO 2000/034784 | 6/2000 |
| WO | WO 2001/064942 | 9/2001 |
| WO | WO 2002/004523 | 1/2002 |
| WO | WO 2002/032925 | 4/2002 |
| WO | WO 2003/002723 | 1/2003 |
| WO | WO 2003/104418 | 12/2003 |
| WO | WO 2004/041863 | 5/2004 |
| WO | WO 2005/040395 | 5/2005 |
| WO | WO 2005/056764 | 6/2005 |
| WO | WO 2005/061018 | 7/2005 |
| WO | WO 2005/118642 | 12/2005 |
| WO | WO 2007/077028 | 7/2007 |
| WO | WO 2007/146959 | 12/2007 |
| WO | WO 2008/031098 | 3/2008 |
| WO | WO 2008/066752 | 6/2008 |
| WO | WO 2008/144610 | 11/2008 |
| WO | WO 2009/023184 | 2/2009 |
| WO | WO 2009/023266 | 2/2009 |
| WO | WO 2009/058379 | 5/2009 |
| WO | WO 2009/062170 | 5/2009 |
| WO | WO 2009/083804 | 7/2009 |
| WO | WO 2009/102421 | 8/2009 |
| WO | WO 2009/133208 | 11/2009 |
| WO | WO 2010/060095 | 5/2010 |
| WO | WO 2011/051333 | 5/2011 |
| WO | WO 2011/073954 | 6/2011 |
| WO | WO 2012/016245 | 2/2012 |
| WO | WO 2012/175741 | 12/2012 |
| WO | WO 2013/024059 | 2/2013 |
| WO | WO 2014/043509 | 3/2014 |

OTHER PUBLICATIONS

Batori et al., "Exploring the Potential of the Monobody Scaffold Effects of Loop Elongation on the Stability of a Fibronectin type III Domain" *Protein Engineering*, Oxford University Press, Surrey, GB 15(12): 1015-1020, Jan. 1, 2002 (XP002996047 ISSN: 0269-2139).
Bloom et al., *Drug Discovery Today* 14(19-20):949-955, 2009.
Bork and Doolittle, "Proposed Acquisition of an Animal Protein by Bacteria" *Proc. Acad. Sci. USA* 89:8990, 1992.
Berman et al., "The Protein Data Bank" *Nucleic Acid Resarch* 28:235-242, 2000.
Better and Horwitz, "Expression of Engineered Antibodies and Antibody Fragments in Microorganisms," *Meth. Enzymol.* 178 476, 1989.
Bird et al., "Single-chain antigen-binding proteins" *Science* 242:423-426, 1988.
Boder et al., "Yeast surface display for screening combinatorial Polypeptide Libraries," *Nature Biotechnology* 15(6):553-557, 1997.
Caldas et al., "Humanization of the Anti-CD18 A ntibody 6.7: an Unexpected Effect of a Framework R esidue in Binding to Antigen" *Mol. lmmunol.* 39(15):941-952 {2003).
Chen et al., "Inhibition of Heregulin Signaling by an Aptamer that Prefentially Binds to the Oligomeric Form of Human Epidermal Growth Factor Receptor-3," *Proc. Natl. Acad. Sci. USA* 100(16):9226-9231,2003.
Chien et al., "Significant Structural and Functional Change of an Antigen-Binding Site by a Distant A mino A cid Substitution: Proposal of a Structural Mechanism," Proc. *Natl. Acad. Sci. USA* 86(14):5532-5536, 1989.

(56) References Cited

OTHER PUBLICATIONS

Cho and Lahey, "Structure of the Extracellular Region of HER3 Reveals and Interdomain Tether," *Science* 297:1330-1333, 2002.
Chothia et al., "Canonical structures for the hypervariable regions of immunoglobulins," *J. Mol. Biol.* 196:901-917, 1987.
Dickinson et al., *Journal of Molecular Biology* 236(4):1079-1092, 1994.
Dutta et al., "High-Affinity Fragment Complementation of a Fibronectin Type III Domain and its Application to Stability Enhancement," *Protein Science* 14(11):2838-2848, 2005.
Dutta et al., "High-throughput analysis of the Protein Sequence-Stability Landscape using a Quantitative Yeast Surface two-hybrid System and Fragment Reconstitution," *J. Mol. Biol.* 382(3):721-733, 2008.
Ferrara et al., "Pathophysiologic Mechanisms of Acute Graft-vs.-Host Disease" *Biol. Blood Marrow Transplant* 5:347-56, 1999.
Garrett et al., "Crystal Structure of a Truncated Epidermal Growth Factor Receptor Extracellular Domain Bound to Transforming Growth Factor Alpha," *Cell* 110:763-773, 2002.
Harding et al., "The Immunogenicity of Humanized and Fully Human Antibodies" mAbs 2(3):256-265, 2010.
Holland et al., "Autoantibodies to Variable Heavy VH Chain Ig Sequences in Humans Impact the Safety and Clinical Pharmacology of a VH Domain Antibody Antagonist of TNF-alpha Receptor 1" *J. Cliff Immunol* 33 (7):1192-1203, 2013.
Huston et al., "Protein Engineering of Antibody Binding Sites: Recovery of Specific Activity in an Anti-Digoxin Single-Chain Fv Analogue Produced in *Escherichia coli*" *Proc. Natl. Acad. Sci USA* 85:5879-5883, 1988.
International Search Report for PCT/EP2009/055365 dated Oct. 19, 2009.
International Search Report for PCT/EP2010/066250 dated Feb. 21, 2011.
International Search Report for PCT/IB2008/003962 dated Feb. 15, 2010.
International Search Report for PCT/US2011/046160 dated Mar. 28, 2012.
International Preliminary Report on Patentablility & Written Opinion for PCT/EP2009/055365 dated Nov. 2, 2010.
International Preliminary Report on Patentablility & Written Opinion for PCT/EP2010/066250 dated Apr. 30, 2012.
International Preliminary Report on Patentablility & Written Opinion for PCT/IB2008/003962 dated Jun. 29, 2010.
International Preliminary Report on Patentablility & Written Opinion for PCT/US2011/046160 dated Feb. 5, 2013.
International Search Report for PCT/US2013/059721 dated Apr. 9, 2014.
Kani et al., "Oligomers of ERBB3 Have Two Distinct Interfaces that Differ in Their Sensitivity to Disruption by Heregulin" *Journal of Biological Chemistry* 280(9):8238-8247, 2005.
Karatan et al., *Chemistry and Biology Current Biology* 11(6):835-844, 2004.
Kohrer et al., "Import and Ochre Suppressors tRNAs into Mammalian Cells" A General Approach to Site-Specific Intersertion of Amino Acid Analogues into Proteins, *Proc. Natl Acad Sci* 98:14310-14315, 2001.
Koide et al., "Monobodies: Antibody Mimics Based on the Scaffold of the fibronectin type III domain." *Methods in Molecular Biology* 352:95-109, 2007.
Koide et al., *Proc. Natl Acad. Sci. USA* 99(3):1253-1258, 2002.
Koide et al., *Journal of Molecular Biology* 284(4):11141-1151, 1998.
Kurachi et al., "Isolation and Characterization of a cDNA Coding for Human factor IX". *PNAS USA* 79:6461-6464, 1982.
Lei et al., "Characterization of the Erwinia Carotovora peIB Gene and its Product Pectate Lyase" *J. Bacteriol* 169:4379, 1987.
Li et al., "Clustering of Highly Homologous Sequences to Reduce the Size of Large Protein Databases" *Bioinformatics* 17(93):282-283, Mar. 2001.
Lipovsek et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," *J. Mol. Biol.*, 368(4):1024-1041, 2007.
Main et al., "The Three-Dimensional Structure of the Tenth Type III Module of Fibronectin: An Insight into RGD-Mediated Interactions" *Cell Press* 71(4):671-678, Nov. 13, 1992.
Meinke et al., "Cellulose-binding polypeptides from Cellulomonas fimi: endoglucanase D (CenD), a family A beta-1,4-glucanase," J. Bacteriol. 175(7):1910, 1993.
Miescher et al., "CHO expression of a novel human recombinant IgGI anti-RhD antibody isolated by phage display," *British Journal of Haematology* 111:157-166, 2000.
Muyldermans, "Single domain camel antibodies: current status " *J. Biotechnol.* 74:277-302, 2001.
Ogiso et al., "Crystal Structure of the Complex Human Epidermal Growth Factor and Receptor Extracellular Domains," *Cell* 110:775-787, 2002.
Parker et al., "Anitbody mimics based on human fibronectin type three domain engineered for thermostability and hig-affinity binding to vascular endothelial growth factor receptor two," *Protein Engineering, Design & Selection* 18(9) 435-444 (2005).
Pluckthun and Skerra, "Expression of functional antibody Fv and Fab fragments in *Escherichia coli.*" *Meth. Enzymol.* 178:497-515, 1989.
Rostagno et al., "Comparison of the fibrin-binding activities in the N-and C-termini of fibronectin," *Biochemical Journal* 338(2):375-386, 1999.
Rudikoff et al.,"Single amino acid substitution altering antigen-binding specificity," *Proc. Natl. Acad. Sci. USA* 79:1979-1983, 1982.
Sayers et al., "5'-3" Exonucleases in Phosphorothioate-Based Oligonucleotide-Directed Mutagenesis" *Nucleic Acids Res.* 16:791-802, 1988.
Shinohara et al. "Structure and chromosomal localization of the human PD-1 gene (PDCD1)" *Genomics* 23(3):704-6, Oct. 1994.
Skerra et al., "The Functional Expression of Antibody Fv Fragments in *Escherichia coli*: Improved Vectors and a Generally Applicable Purification Technique" *Nature Biotechnology* 9:273-278, 1991.
Staunton et al., "Preparation of recombinant fibronectin fragments for functional and structural studies," *Methods in Molecular Biology* 522:73-99, 2009.
Urso et al, "Differences in Signaling Properties of the Cytoplasmic Domains of the Insulin Receptor and Insulin-like Growth Factor Receptor in 3T3-L1 Adipocytes" *J. of Bio. Chem* 274(43):30864-30873, 1999.
Wang et al., "Regulation of glucose transporters and hexose uptake in 3T3-L1 adipocytes: glucagon-like peptide-1 and insulin interactions" *J. Mole. Endo.* 19:241-248, 1997.
Winkler et al., "Changing the antigen binding specificity by single point mutations of an anti-p24 (HIV-1) antibody," *J. Imm.* 265:4505-4514, 2000.
Written Opinion for PCT/EP2011/057200 dated Jul. 29, 2011.
Xu et al., "Directed evolution of high-affinity antibody ninnies using mRNA display," *Chemistry and Biology* 9:933-942, 2002.

* cited by examiner

AB Loop
*Loop length distribution*

| Loop Length | Number Sequences | Percent of Sequences |
|---|---|---|
| 1 | 90 | 0.72 |
| 2 | 97 | 0.78 |
| 3 | 12,265 | 98.50 |

Fig. 3B

AB Loop

*Positional distribution of loop length 3 (12,265 sequences)*

| AB Loop Length 3 | | Top 7 Amino Acid Abundance (%) | | | | | | |
|---|---|---|---|---|---|---|---|---|
| Position | Amino Acids | 1st | 2nd | 3rd | 4th | 5th | 6th | 7th |
| 1 | TSGNDKQ | 35.4 | 21.6 | 10.9 | 6.1 | 5.8 | 2.9 | 2.9 |
| 2 | SAKPDET | 16.6 | 12.6 | 12.2 | 11.4 | 8.7 | 8.1 | 5.7 |
| 3 | TDSNERG | 23.5 | 18.1 | 14.4 | 14.2 | 6.5 | 5.9 | 3.4 |

*Fig. 4A*

CD Loop
*Loop length distribution*

| Loop Length | Number Sequences | Percent of Sequences |
|---|---|---|
| 4 | 404 | 3.24 |
| 5 | 1,937 | 15.56 |
| 6 | 5,054 | 40.59 |
| 7 | 2,615 | 21.00 |
| 8 | 1,161 | 9.32 |
| 9 | 866 | 6.95 |
| 10 | 415 | 3.33 |

*Fig. 5B*

CD Loop

Positional distribution of loop length 5 (1,937 sequences)

| CD Loop Length 5 | | Top 7 Amino Acid Abundance (%) | | | | | | |
|---|---|---|---|---|---|---|---|---|
| Position | Amino Acids | 1st | 2nd | 3rd | 4th | 5th | 6th | 7th |
| 1 | GTASERK | 13.8 | 12.8 | 10.3 | 8.5 | 7.6 | 7.6 | 7.2 |
| 2 | DGNSEQT | 25.7 | 18.9 | 12.7 | 9.3 | 7.3 | 5.5 | 4.5 |
| 3 | GSKDATN | 49.4 | 7.7 | 5.8 | 5.6 | 4.6 | 4.4 | 4.3 |
| 4 | QSGVETK | 15.5 | 11.0 | 10.5 | 7.7 | 7.1 | 6.7 | 6.1 |
| 5 | PWETSVL | 17.3 | 10.7 | 10.7 | 7.8 | 7.3 | 7.2 | 5.9 |

FIG. 6A

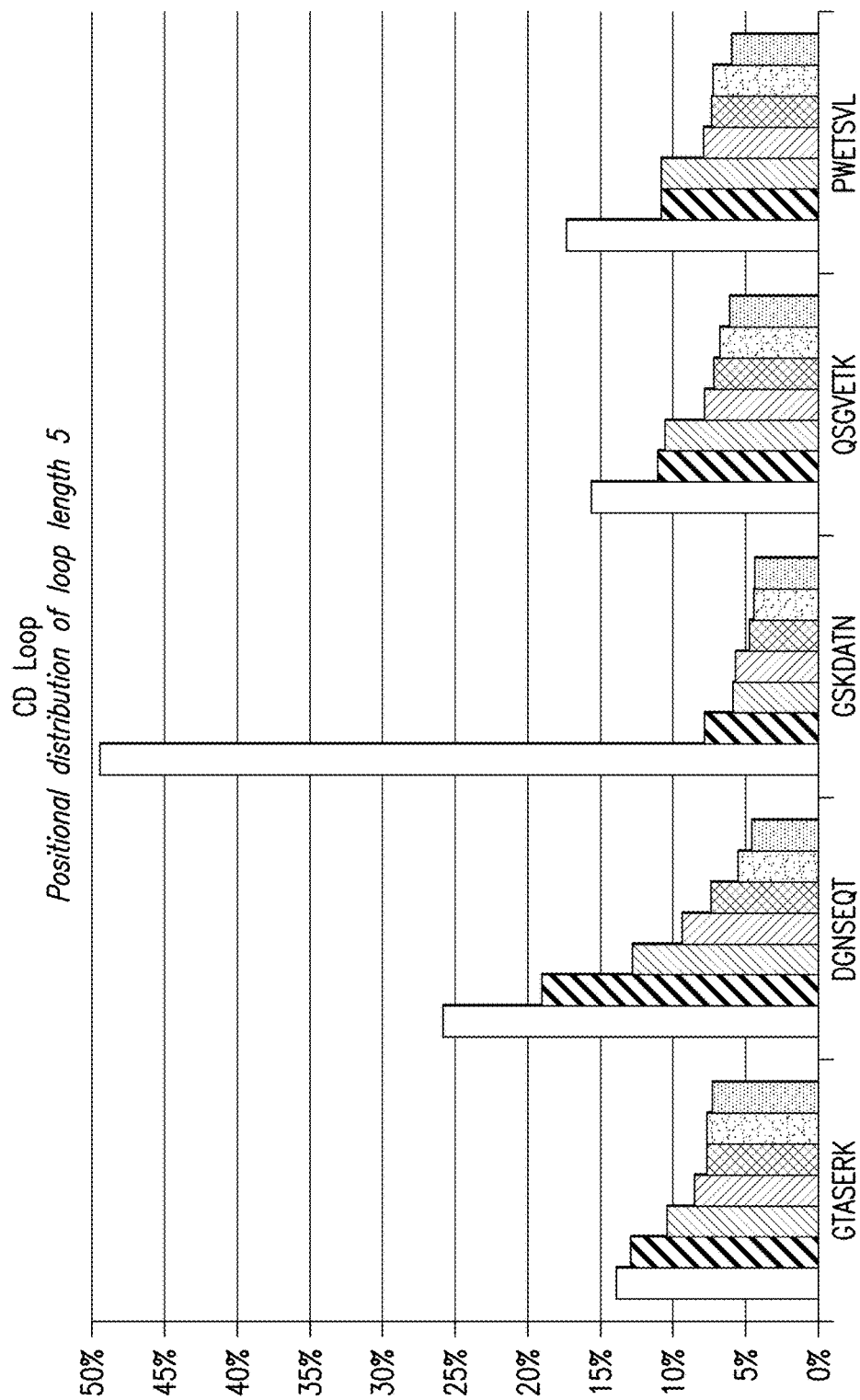

CD Loop

Positional distribution of loop length 6 (5,054 sequences)

| CD Loop Length 6 | | Top 7 Amino Acid Abundance (%) | | | | | | |
|---|---|---|---|---|---|---|---|---|
| Position | Amino Acids | 1st | 2nd | 3rd | 4th | 5th | 6th | 7th |
| 1 | KTAVSLE | 17.2 | 12.0 | 10.2 | 9.9 | 7.6 | 6.7 | 6.3 |
| 2 | GDSNETK | 23.1 | 12.4 | 11.3 | 9.7 | 7.9 | 7.1 | 5.7 |
| 3 | STGREDA | 20.5 | 14.8 | 13.7 | 10.2 | 7.4 | 7.0 | 5.4 |
| 4 | GEDTKNS | 17.8 | 10.5 | 9.0 | 7.7 | 7.1 | 6.8 | 6.5 |
| 5 | ERTKDAQ | 15.5 | 10.5 | 10.3 | 8.0 | 7.8 | 6.3 | 5.8 |
| 6 | WEPTAYS | 59.1 | 5.6 | 4.2 | 3.7 | 3.0 | 2.9 | 2.5 |

FIG. 7A

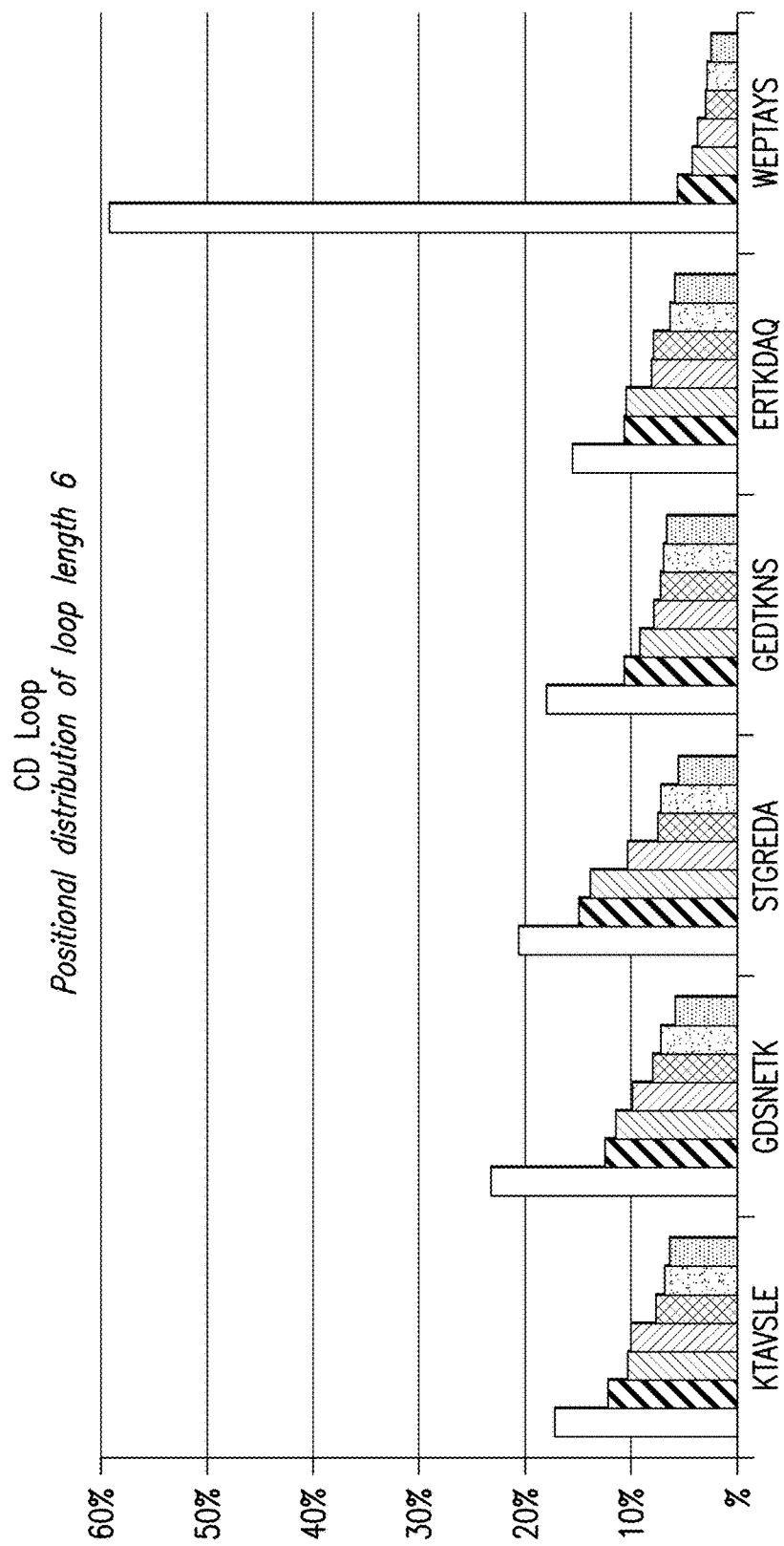

CD Loop

*Positional distribution of loop length 7 (2,615 sequences)*

| CDL Position | Amino Acids | Top 7 Amino Acid Abundance (%) | | | | | | |
|---|---|---|---|---|---|---|---|---|
| | | 1st | 2nd | 3rd | 4th | 5th | 6th | 7th |
| 1 | KAETSVG | 18.5 | 13.6 | 11.9 | 9.8 | 7.9 | 7.9 | 4.7 |
| 2 | GNDSETK | 20.1 | 15.5 | 13.3 | 10.6 | 7.9 | 7.4 | 5.1 |
| 3 | GSETAKD | 19.1 | 14.6 | 9.7 | 9.0 | 7.5 | 6.7 | 6.5 |
| 4 | GEPTSDK | 13.7 | 13.3 | 11.2 | 9.7 | 7.1 | 6.7 | 5.9 |
| 5 | GESDTRA | 16.6 | 13.4 | 10.3 | 8.6 | 6.7 | 6.5 | 6.3 |
| 6 | EWPDYTA | 17.4 | 13.1 | 11.3 | 7.5 | 7.2 | 6.0 | 5.9 |
| 7 | TWVEASP | 13.6 | 13.3 | 10.5 | 8.6 | 7.1 | 7.0 | 5.7 |

*Fig. 8A*

EF Loop
*Loop length distribution*

| Loop Length | Number Sequences | Percent of Sequences |
|---|---|---|
| 3 | 4 | 0.03 |
| 4 | 3 | 0.02 |
| 5 | 83 | 0.67 |
| 6 | 12,306 | 98.83 |
| 7 | 33 | 0.27 |
| 8 | 22 | 0.18 |
| 9 | 1 | 0.01 |

*Fig. 9A*

EF Loop

Positional distribution of loop length 6 (12,306 sequences)

| CD Loop Length EF | | Top 7 Amino Acid Abundance (%) | | | | | | |
|---|---|---|---|---|---|---|---|---|
| Position | Amino Acids | 1st | 2nd | 3rd | 4th | 5th | 6th | 7th |
| 1 | GNDKESR | 40.0 | 18.0 | 14.3 | 6.8 | 4.7 | 4.6 | 3.2 |
| 2 | LVIMTFA | 92.1 | 2.5 | 1.7 | 1.5 | 0.7 | 0.5 | 0.3 |
| 3 | KTEQLSI | 14.0 | 13.5 | 12.2 | 8.1 | 6.9 | 6.8 | 6.8 |
| 4 | PEAKSTN | 46.2 | 17.5 | 6.8 | 6.0 | 4.3 | 3.7 | 2.4 |
| 5 | GNDASYF | 45.5 | 13.1 | 8.6 | 5.8 | 5.5 | 4.9 | 3.2 |
| 6 | TVSKRAH | 37.9 | 8.6 | 7.7 | 7.4 | 6.2 | 5.8 | 4.5 |

FIG. 10A

UNIVERSAL FIBRONECTIN TYPE III BOTTOM-SIDE BINDING DOMAIN LIBRARIES

CROSS-REFERENCE TO RELATED APPLICATIONS

This application is a continuation of U.S. application Ser. No. 13/504,824, filed Apr. 27, 2012, which is a US National Phase 371 application of PCT/EP2010/066250, which has an international filing date Oct. 27, 2010, which claims benefit of U.S. Application Ser. No. 61/256,409, filed Oct. 30, 2009, the disclosures of which are hereby incorporated by reference.

SEQUENCE LISTING

The instant application contains a Sequence Listing which has been submitted electronically in ASCII format and is hereby incorporated by reference in its entirety. Said ASCII copy, created on Oct. 19, 2017, is named PAT053902-US-PCT_SEQ_LISTING_updated_2017-10-19.TXT and is 10000 bytes in size.

BACKGROUND OF THE INVENTION

Scaffold based binding proteins are becoming legitimate alternatives to antibodies in their ability to bind specific ligand targets. These scaffold binding proteins share the quality of having a stable framework core that can tolerate multiple substitutions in the ligand binding regions. Some scaffold frameworks have immunoglobulin like protein domain architecture with loops extending from a beta sandwich core. A scaffold framework core can then be synthetically engineered from which a library of different sequence variants can be built upon. The sequence diversity is typically concentrated in the exterior surfaces of the proteins such as loop structures or other exterior surfaces that can serve as ligand binding regions.

Fibronectin Type III domain (Fn3) was first identified as a one of the repeating domains in the fibronectin protein. The Fn3 domain constitutes a small (~94 amino acids), monomeric β-sandwich protein made up of seven (3 strands with three connecting loops. The three loops near the N-terminus of Fn3, are functionally analogous to the complementarity-determining regions of immunoglobulin domains. Fn3 loop libraries can then be engineered to bind to a variety of targets such as cytokines, growth factors and receptor molecules and other proteins.

One potential problem in creating these synthetic libraries is the high frequency of unproductive variants leading therefore, to inefficient candidate screens. For example, creating diversity in the variants often involves in vitro techniques such as random mutagenesis, saturation mutagenesis, error-prone PCR, and gene shuffling. These strategies are inherently stochastic and often require the construction of exceedingly large libraries to comprehensively explore sufficient sequence diversity. Additionally, there is no way to enumerate the number, what type and where in the protein the mutations have occurred. Furthermore, these random strategies create indiscriminate substitutions that cause protein architecture destabilization. It has been shown that improvement in one characteristic, such as affinity optimization, usually leads to decreased thermal stability when compared to the original protein scaffold framework.

Accordingly, a need exists for a fibronectin binding domain library that is systematic in construction. By bioinformatics led design, the loop candidates are flexible for insertion into multiple Fn3 scaffolds. By specific targeted loop substitutions, overall scaffold stability is maximized while concurrently, non-immunogenic substitutions are minimized. Additionally, the library can be size tailored so that the overall diversity can be readily screened in different systems. Furthermore, the representative diversity of the designed loops are still capable of binding a number of pre-defined ligand targets. Moreover, the systematic design of loop still allows subsequent affinity maturation of recovered binding clones.

SUMMARY OF THE INVENTION

In one aspect, the invention includes a natural-variant combinatorial library of fibronectin Type 3 domain (Fn3) polypeptides useful in screening for the presence of one or more polypeptides having a selected binding or enzymatic activity. The library polypeptides include (a) regions A, AB, B, C, CD, D, E, EF, F, and G having wildtype amino acid sequences of a selected native fibronectin Type 3 polypeptide or polypeptides, and (b) loop regions AB, CD, and EF having selected lengths (Bottom Loops). The Fn3 may also have loop regions BC, DE, and FG having wildtype amino acid sequences, having selected lengths (Top Loops), or mutagenized amino acid sequences.

Accordingly, in one aspect, the invention pertains to a method of forming a library of fibronectin Type 3 (Fn3) domain polypeptides useful in screening for the presence of one or more polypeptides having a selected binding or enzymatic activity. The method comprises (i) aligning AB, CD, and EF amino acid loop sequences in a collection of native fibronectin Type 3 domain polypeptides, (ii) segregating the aligned loop sequences according to loop length, (iii) for a selected loop and loop length from step (ii), performing positional amino acid frequency analysis to determine the frequencies of amino acids at each loop position, (iv) for each loop and loop length analyzed in step (iii), identifying at each position a conserved or selected semi-conserved consensus amino acid and other natural-variant amino acids, (v) for at least one selected loop and loop length, forming: (1) a library of mutagenesis sequences expressed by a library of coding sequences that encode, at each loop position, the consensus amino acid, and if the consensus amino acid has a occurrence frequency equal to or less than a selected threshold frequency of at least 50%, a single common target amino acid and any co-produced amino acids, or (2) a library of natural-variant combinatorial sequences expressed by a library of coding sequences that encode at each loop position, a consensus amino acid and, if the consensus amino acid has a frequency of occurrence equal to or less than a selected threshold frequency of at least 50%, other natural variant amino acids, including semi-conserved amino acids and variable amino acids whose occurrence rate is above a selected minimum threshold occurrence at that position, or their chemical equivalents, (vi) incorporating the library of coding sequences into framework Fn3 coding sequences to form an Fn3 expression library, and (vi) expressing the Fn3 polypeptides of the expression library.

The library may have a given threshold is 100%, unless the loop amino acid position contains only one dominant and one variant amino, and the dominant and variant amino are chemically similar amino acids, in which case the given threshold may be 90%. In this embodiment, the library contains all natural variants or their chemical equivalents having at least some reasonable occurrence frequency, e.g., 10%, in the in the selected loop and loop position.

The natural-variant combinatorial sequences may be in a combination of loops and loop lengths selected from loops AB and CD, AB and EF, and CD and EF, where the AB loop comprises 1-3 amino acids (AB/1-3), and preferably 3 amino acids (AB/3); the CD loop comprises 4-10 amino acids (CD/4-10), and preferably 5, 6, or 7 amino acids (CD/5, CD/6, CD/7); and the EF loop comprises 3-9 amino acids (EF/3-9), and preferably 6 amino acids (EF/6). The natural-variant combinatorial sequences may be in a combination of loops and loop lengths selected from the group consisting of AB/1-3, AB/3, CD/4-10, CD/5, CD/6, CD/7 and EF/3-9, EF/6.

The library may have at two of the loop combinations AB and CD, AB and EF, and CD and EF, beneficial mutations identified by screening a natural-variant combinatorial library containing amino acid variants in the two loop combination, and at the third loop, identified by AB, CD, and EF, respectively.

In one embodiment, the library may have the wildtype amino acid sequences in regions A, AB, B, C, CD, D, E, EF, F, and G of the 10th fibronectin Type III module of human fibronectin. In another embodiment, the library may have the wildtype amino acid sequences in regions A, AB, B, C, CD, D, E, EF, F, and G of the 14th fibronectin Type III module of human fibronectin.

In another aspect, the invention pertains to a library of fibronectin Type 3 (Fn3) domain polypeptides useful in screening for the presence of one or more polypeptides having a selected binding or enzymatic activity, said polypeptides. The library comprises (a) regions A, AB, B, C, CD, D, E, EF, F, and G having wildtype amino acid sequences of a selected native fibronectin Type 3 polypeptide, and (b) loop regions AB, CD, and EF having selected lengths, where at least one selected loop region of a selected length contains a library of mutagenesis sequences expressed by a library of coding sequences that encode, at each loop position, a conserved or selected semi-conserved consensus amino acid and, if the consensus amino acid has an occurrence frequency equal to or less than a selected threshold frequency of at least 50%, a single common target amino acid and any co-produced amino acids.

In another aspect the invention pertains to a natural-variant combinatorial library of fibronectin Type 3 (Fn3) domain polypeptides useful in screening for the presence of one or more polypeptides having a selected binding or enzymatic activity. The polypeptides comprise (a) regions A, AB, B, C, CD, D, E, EF, F, and G having wildtype amino acid sequences of a selected native fibronectin Type 3 polypeptide, and (b) loop regions AB, CD, and EF having selected lengths, where at least one selected loop region of a selected length contains a library of natural-variant combinatorial sequences expressed by a library of coding sequences that encode at each loop position, a conserved or selected semi-conserved consensus amino acid and, if the consensus amino acid has a frequency of occurrence equal to or less than a selected threshold frequency of at least 50%, other natural variant amino acids, including semi-conserved amino acids and variable amino acids whose occurrence rate is above a selected minimum threshold occurrence at that position, or their chemical equivalents.

The library has a library of natural-variant combinatorial sequences at a combination of loops and loop lengths selected from loops AB and CD, AB and EF, and CD and EF, where the AB loop is selected from one of AB/1-3, AB/3, and CD/4-10, CD/5, CD/6, CD/7 the AB/1-3, AB/3, and EF/3-9, EF/6, CD/4-10, CD/5, CD/6, CD/7 and EF/3-9, EF/6, or a combination of all three loops selected from the group consisting of AB/1-3, AB/3, CD/4-10, CD/5, CD/6, CD/7, EF/3-9, and EF/3. The library has a given threshold is 100%, unless the loop amino acid position contains only one dominant and one variant amino, and the dominant and variant amino have side chains with similar physiochemical properties, in which case the given threshold is 90%. The polypeptides have the wildtype amino acid sequences in beta-strand regions A, AB, B, C, CD, D, E, EF, F, and G of the 10th fibronectin Type III module of human fibronectin, or 14th fibronectin Type III module of human fibronectin.

In one embodiment, the library has an AB loop length of 3. In another embodiment, the library has a CD loop length of 5, 6, or 7. In another embodiment, the library has an EF loop length of 6. The polypeptides of the library are encoded by an expression library selected from the group consisting of a ribosome display library, a polysome display library, a phage display library, a bacterial expression library, and a yeast display library.

In another aspect, the invention pertains to an expression library of polynucleotides encoding the library of polypeptides and is produced by synthesizing polynucleotides encoding one or more beta-strand framework regions and one or more loop regions wherein the polynucleotides are predetermined, wherein the polynucleotides encoding said regions further comprise sufficient overlapping sequence whereby the polynucleotide sequences, under polymerase chain reaction (PCR) conditions, are capable of assembly into polynucleotides encoding complete fibronectin binding domains.

In yet another aspect, the invention pertains to a method of identifying a polypeptide having a desired binding affinity with respect to a selected antigen. The method comprises reacting the natural-variant combinatorial library of Fn3 polypeptides with the selected antigen, and screening the Fn3 polypeptides to select those having a desired binding affinity with respect to the selected antigen. The method further comprises the step of identifying the polynucleotide that encodes the selected fibronectin binding domain.

BRIEF DESCRIPTION OF FIGURES

FIG. 3B is a table showing loop length distribution in the AB loop length, showing 3 is the single most predominant size seen in expressed Fn3 sequences.

FIG. 4A is a table showing the positional distribution of amino acids at positions 1, 2 and 3 of an AB loop length size 3 and the top 7 amino acid abundance percentages of the amino acid at each position (SEQ ID NOs. 2-4).

FIG. 5B is a table showing loop length distribution in the CD loop length, CD loop lengths 5, 6 and 7 are the most predominant sizes seen in expressed Fn3 sequences.

FIG. 6A is a table showing the positional distribution of amino acids at positions 1, 2, 3, 4, and 5 of the CD loop length size 5 and the top 7 amino acid abundance percentages of the amino acids at each position (SEQ ID NOs. 5-9).

FIG. 6B is a bar graph showing sequence diversity of an exemplary loop region in the form of amino acid variability profile (frequency distribution) for the CD loop length size 5 (SEQ ID NOs. 5-9).

FIG. 7A is a table showing the positional distribution of amino acids at positions 1, 2, 3, 4, 5, and 6 of the CD loop length size 6 and the top 7 amino acid abundance percentages of the amino acids at each position (SEQ ID NOs. 10-15).

FIG. 7B is a bar graph showing sequence diversity of an exemplary loop region in the form of amino acid variability profile (frequency distribution) for the CD loop length size 6 (SEQ ID NOs. 10-15).

FIG. 8A is a table showing the positional distribution of amino acids at positions 1, 2, 3, 4, 5, 6, and 7 of the CD loop length size 7 and the top 7 amino acid abundance percentages of the amino acids at each position (SEQ ID NOs. 16-22).

FIG. 9A is a table showing loop length distribution in the EF loop length, showing 6 is the single most predominant size seen in expressed Fn3 sequences.

FIG. 10A is a table showing the positional distribution of amino acids at positions 1, 2, 3, 4, 5, and 6 of an EF loop length size 6 and the top 7 amino acid abundance percentages of the amino acid at each position (SEQ ID NOs. 23-28).

DETAILED DESCRIPTION OF THE INVENTION

Definitions

Figure 2:
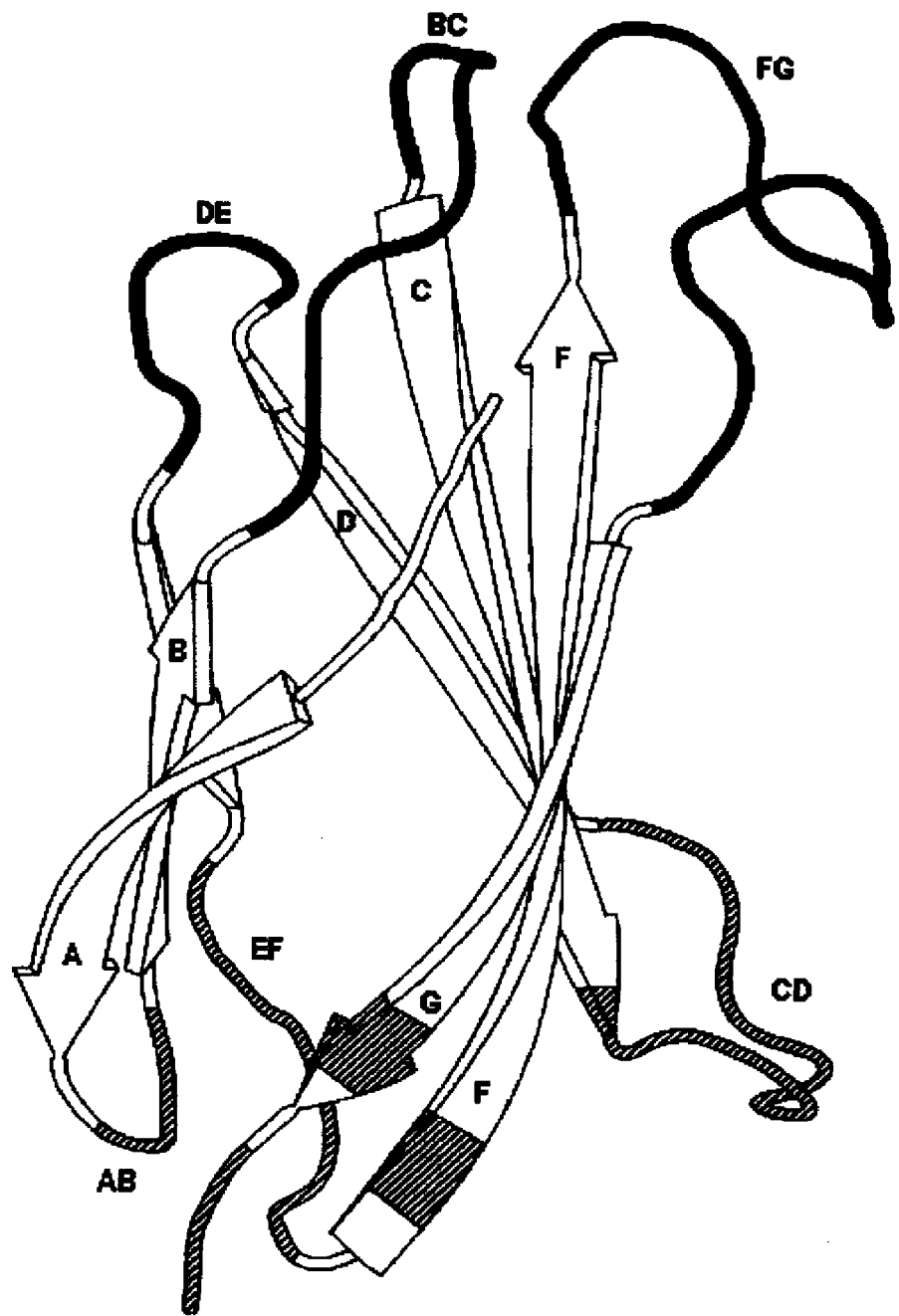
FIG. 2 depicts a schematic showing the top and bottom loop faces of Fn3 illustrating the two antiparallel beta-sheets domain. One half is composed of beta strands (ABE) and the other half is composed of (CDFG). The 6 CDR like loops are also indicated: AB, BC, CD, DE, EF, and FG. Loops BC, DE and FG are present at the N-terminus of the Fn3 domain and are arranged to form ligand binding surfaces. The RGD sequence is located in the FG loop.

The terms below have the following meanings unless indicated otherwise in the specification:

As used herein, the term "Fibronectin type III domain" or "Fn3 domain" refers to a wild-type Fn3 domain from any organism, as well as chimeric Fn3 domains constructed from beta strands from two or more different Fn3 domains. As is known in the art, naturally occurring Fn3 domains have a beta-sandwich structure composed of seven beta-strands, referred to as A, B, C, D, E, F, and G, linked by six loops, referred to as AB, BC, CD, DE, EF, and FG loops (See e.g., Bork and Doolittle, Proc. Natl. Acad. Sci. U.S.A 89:8990, 1992; Bork et al., Nature Biotech. 15:553, 1997; Meinke et al., J. Bacteriol. 175:1910, 1993; Watanabe et al., J. Biol. Chem. 265:15659, 1990; Main et al., 1992; Leahy et al., 1992; Dickinson et al., 1994; U.S. Pat. No. 6,673,901; Patent Cooperation Treaty publication WO/03104418; and, US patent application 2007/0082365, the entire teachings of which are incorporated herein by reference). Three loops are at the top of the domain (the BC, DE and FG loops) and three loops are at the bottom of the domain (the AB, CD and EF loops) (FIG. 2). In a particular embodiment, of the invention, the Fn3 domain is from the tenth Fn3 domain of human Fibronectin ($^{10}$Fn3) (SEQ ID NO. 1). Individual Fn3 domain polypeptides are referred to by module number and protein name, e.g., the 10th or 14th module of human fibronectin ($^{10}$Fn or $^{14}$Fn).

As used herein the term "Fn3-based binding molecule" or "fibronectin type III (Fn3)-based binding molecule" refers to an Fn3 domain that has been altered to contain one or more non-Fn3 binding sequences. In a particular embodiment, one or more of the bottom AB, CD and/or EF loops are altered compared to the corresponding wild-type Fn3 domain to contain one or more non-Fn3-binding sequences. In another embodiment, one or more of the bottom AB, CD or EF loops and one or more of the top BC, DE and FG loops are altered compared to the corresponding wild-type Fn3 domain to contain one or more non-Fn3-binding sequences. Such molecules are referred to herein as "bispecific Fn3-based binding molecules". In a further embodiment, two or more Fn3-based binding molecules or bispecific Fn3-based binding molecule are linked together. Such molecules are referred to herein as "multispecific Fn3-based binding molecules". (see e.g., U.S. Ser. No. 61/050,142 incorporated herein by reference.)

The term "non-Fn3 binding sequence" refers to an amino acid sequence which is not present in the naturally occurring (e.g., wild-type) Fn3 domain, and which binds to a specific target. Such non-Fn3 binding sequences are typically introduced by modifying (e.g., by substitution and/or addition) the wild-type Fn3 domain (e.g., within the bottom loops and/or top loop regions). This can be achieved by, for example, random or predetermined mutation of amino acid residues within the wild-type Fn3 domain.

The term "monospecific" as used herein refers to an Fn3-based binding molecule that binds to one or more target molecules comprising Fn3 domains in which only the bottom region of the Fn3 domain, or the top region of the Fn3 domain, but not both, are used for binding. For example, a bottom monospecific Fn3-based binding molecule is one that uses only the bottom loops, such as the AB, CD, or EF loops, or C-terminal of the Fn3 domain to bind a target, while a top monospecific Fn3-based binding molecule uses only the top loops of the Fn3 domain, such as BC, DE, and FG loops, to bind the target. It is to be understood that not all three loops from the top or bottom region need to be used for binding the target molecule.

The monospecific Fn3 domains can also be linked together (e.g., in a pearl-like fashion) to form a multispecific Fn3-based binding molecules that comprises, for example, at least two monospecific Fn3 domains that are linked together. For bottom monospecific binding molecules, each of the Fn3 domains uses at least one bottom loop or C-terminal region to bind to one or more target molecules. In one embodiment, this multispecific Fn3-based binding molecule binds to different target regions of a same target molecule (e.g., Target A). For example, one Fn3 domain can bind to a first target region of Target A and another Fn3 domain can bind to a second target region of Target A. This can be used to increase avidity of the Fn3-based binding molecule for the target molecule. In another embodiment, the multispecific Fn3-based binding molecule binds to multiple target molecules. For example, one Fn3 domain can bind to Target A and a another Fn3 domain can bind to Target B (e.g., a half life extender). In yet another embodiment, the multispecific Fn3-based binding molecule comprises at least two monospecific Fn3 domains that bind to different target regions of Target A and at least two monospecific Fn3 domains that bind to different target regions of Target B. The skilled artisan will appreciate that any number of Fn3 domains can be linked in this fashion to create a multispecific Fn3-based binding molecule that are able to bind to different target regions of the same target molecule or different target molecules.

The term "bispecific" as used herein refers to an Fn3-based binding molecule that binds to one or more targets using both the bottom region of the Fn3 domain and the top region of the Fn3 domain. For example a bispecific Fn3-based binding molecule comprises Fn3 domains that use both the bottom loops, such as the AB, CD, or EF loops, or C-terminal of the molecule and the top loops of the molecule, such as BC, DE, and FG loops, to bind the target. The bispecific Fn3-based binding molecules can be used to bind the same target molecule, e.g., Target A, which can bind to both the top and bottom of the bispecific Fn3-based binding molecule (See FIG. 3b). Alternatively, the bispecific Fn3-based binding molecule can be used to bind to two different target molecules, e.g., Target A and Target B. In this instance, the top loops can be used to bind to Target A and the bottom loops can be used to bind to Target B, or vice versa (See FIG. 3b). The bispecific Fn3-based binding molecules can also be linked together (e.g., in a pearl-like fashion) to form a multispecific Fn3-based binding molecules.

The term "multispecific" as used herein refers to a Fn3-based binding molecule that comprises at least two monospecific Fn3-based binding molecules linked together or at least two bispecific Fn3-based binding molecules linked together.

The term "complementarity determining region (CDR)" refers to a hypervariable loop from an antibody variable domain or from a T-cell receptor. The position of CDRs within a antibody variable region have been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al., J. Mol. Biol. 196:901-917, 1987, which are incorporated herein by reference).

The term "single domain antibodies" refers to any naturally-occurring single variable domain and corresponding engineered binding fragments, including human domain antibodies as described by Domantis (Domantis/GSK (Cambridge, UK) or camelid nanobodies as defined hereafter.

The term "single chain antibody" refers to an antigen binding portion of a light chain variable region and an antigen binding portion of a heavy chain variable region, joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. U.S.A 85:5879-5883).

The term "SCALP" refers to a Single-Chain Antibody-like Protein. The grouping SCALP includes an isolated heavy chain of an antibody, or fragment, thereof; or one variable region fused to another. Thus, the group of SCALPS includes $V_{HH}$ (NANOBODY); and $V_{HH}$ plus any one or more constant region of the heavy chain (e.g., CH1, CH2, and/or CH3). Thus, a SCALP is exemplified by a $V_{HH}$; a $V_{HH}$ CH1; a $V_{HH}$+CH2; a $V_{HH}$+CH3; a $V_{HH}$+CH1+CH2; a $V_{HH}$+CH1+CH2+CH3; a $V_{HH}$+CH2+CH3; a $V_{HH}$+CH1+CH3; etc. SCALPs include single domain antibodies.

The term "NANOBODY®" refers to a region of camelid antibody which is the small single variable domain devoid of light chain and that can be obtained by genetic engineering to yield a small protein having high affinity for a target, resulting in a low molecular weight antibody-derived protein. See WO07042289 and U.S. Pat. No. 5,759,808 issued Jun. 2, 1998; see also Stijlemans, B. et al., 2004. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the NANOBODY® can be "humanized". Thus the natural low antigenicity of camelid antibodies to humans can be further reduced.

The term "SmALP" refers to any Small Antibody-like Protein. SmALPs include Fab fragments, which comprise the VH, CH, VL and VH portions; Fv, which comprise the VH and VL portions; ScFv, which comprise a VH and VL portion fused to each other; dAbs; di-ScFv, which comprise two ScFv fragments; and Fcabs. These and other SmALPs are described in Classical and Heavy Chain Antibodies, from Muyldermans, S. (2001), J Biotechnol. 74, 277-302, and are well-known in the art. dAbs (domain antibodies) correspond to the variable regions of either the heavy (VH) or light (VL) chains of human antibodies and have a molecular weight of approximately 13 kDa, or less than one-tenth the size of a full antibody. dAbs are available from Domantis Limited, a wholly owned subsidiary of GlaxoSmithKline. An Fcab (antigen-binding Fc) is a compressed antibody, comprising a CH2 and CH3 domain, with two identical antigen binding sites engineered into the CH3 domains, as available from f-star Biotechnologische Forschungs- and Entwicklungsges, M.b.H. A ASCP-body of the present invention can be fused to a CH1 and/or CH2 and/or CH3, and/or VL region. The ASCP-body can thus be within the context of a SCALP or SmALP.

The term "target" refers to an antigen or epitope recognized by Fn3-based binding molecule of the invention. Targets include, but are not limited to, epitopes present on proteins, peptides, carbohydrates, and/or lipids.

The term "conjugate" refers to an Fn3-based binding molecule chemically or genetically linked to one or more non-Fn3 moieties.

The term "non-Fn3 moiety" refers to a biological or chemical entity that imparts additional functionality to a molecule to which it is attached. In a particular embodiment, the non-Fn3 moiety is a polypeptide, e.g., human serum albumin (HSA), or a chemical entity, e.g., polyethylene gycol (PEG) which increases the half-life of the Fn3-based binding molecule in vivo.

The term "library" of Fn3 polypeptides refers to a collection of Fn3 polypeptides having a selected sequence variation or diversity in at least one of the AB, CD, and EF loops of a defined length. The term "library" is also used to refer to the collection of amino acid sequences within a selected AB, CD, and EF loop of a selected length, and to the collection of coding sequences that encode loop or polypeptide amino acid libraries.

The term "universal Fn3 bottom-side binding library" refers to a Fn3 polypeptide library in which amino acid diversity in one or more of the AB, CD, and EF loop regions is determined by or reflects the amino acid variants present in a collection of known Fn3 sequences.

The term "universal N+– binding library" or "N+/– libraries" refers to a more sophisticated or fine tuned library in which the most frequent amino acids surrounding an fixed amino acid are determined in the library design. These N+/– libraries are constructed with variations in bottom loops, AB, CD, and EF, the top loops, BC, DE, FG, or any combination of top and bottom loops. For "N+/– libraries," N is the most predominant amino acid at a particular position and amino acids upstream or downstream are designated +N or —N, respectively. For example, N+3 is an amino acid 3 positions upstream of N, while N–3 is an amino acid 3 positions downstream of N in a 3D structure of Fn3. Likewise, N+2 and N+1 are amino acids at positions 2 and 1 upstream of N, respectively, while N–2 and N–1 are amino acids at positions 2 and 1 downstream of N, respectively. By altering, N from the most predominantly abundant amino acid to a less abundant amino acid, the effect of that modification can be assessed on the abundance of amino acids at 1, 2, or 3 positions away from N. In designing such a library, the frequency and abundance of amino acids surrounding the fixed N position are determined. These differences can be used to generate universal fibronectin bottom-side binding domain libraries, top-side binding domain libraries, or a combination of both bottom-side and top-side binding domain libraries.

The term "conserved amino acid residue" or "fixed amino acid" refers to an amino acid residue determined to occur with a frequency that is high, typically at least 50% or more (e.g., at about 60%, 70%, 80%, 90%, 95%, or 100%), for a given residue position. When a given residue is determined to occur at such a high frequency, i.e., above a threshold of about 50%, it may be determined to be conserved and thus represented in the libraries of the invention as a "fixed" or "constant" residue, at least for that amino acid residue position in the loop region being analyzed.

The term "semi-conserved amino acid residue" refers to amino acid residues determined to occur with a frequency that is high, for 2 to 3 residues for a given residue position. When 2-3 residues, preferably 2 residues, that together, are represented at a frequency of about 40% of the time or higher (e.g., 50%, 60%, 70%, 80%, 90% or higher), the residues are determined to be semi-conserved and thus represented in the libraries of the invention as a "semi-fixed" at least for that amino acid residue position in the loop region being analyzed. Typically, an appropriate level of nucleic acid mutagenesis/variability is introduced for a semi-conserved amino acid (codon) position such that the 2 to 3 residues are properly represented. Thus, each of the 2 to 3 residues can be said to be "semi-fixed" for this position. A "selected semi-conserved amino acid residue" is a selected one of the 2 or more semi-conserved amino acid residues, typically, but not necessarily, the residue having the highest occurrence frequency at that position.

The term "variable amino acid residue" refers to amino acid residues determined to occur with a lower frequency (less than 20%) for a given residue position. When many residues appear at a given position, the residue position is determined to be variable and thus represented in the libraries of the invention as variable at least for that amino acid residue position in the loop region being analyzed. Typically, an appropriate level of nucleic acid mutagenesis/variability is introduced for a variable amino acid (codon) position such that an accurate spectrum of residues are properly represented. Of course, it is understood that, if desired, the consequences or variability of any amino acid residue position, i.e., conserved, semi-conserved, or variable, can be represented, explored or altered using, as appropriate, any of the mutagenesis methods disclosed herein. A lower threshold frequency of occurrence of variable amino acids may be, for example, 5-10% or lower. Below this threshold, variable amino acids may be omitted from the natural-variant amino acids at that position.

The term "consensus" refers to an amino acid in a AB, CD, and EF loop of an Fn3 polypeptide is a conserved amino acid or a selected one of a semi-conserved amino acids that appears predominantly at a position within the loop.

The term "natural-variant amino acids" includes conserved, semi-conserved, and variable amino acid residues observed, in accordance with their occurrence frequencies, at a given position in a selected loop of a selected length. The natural-variant amino acids may be substituted by chemically equivalent amino acids, and may exclude variable amino acid residues below a selected occurrence frequency, e.g., 5-10%, or amino acid residues that are chemically equivalent to other natural-variant amino acids.

The term "library of mutagenesis sequences" refers to a library of sequences within a selected Fn3 loop and loop length which is expressed by a library of coding sequences that encode, at each loop position, a conserved or selected semi-conserved consensus amino acid and, if the consensus amino acid has an occurrence frequency equal to or less than a selected threshold frequency of at least 50%, a single common target amino acid and any co-produced amino acids. Thus, for each of target amino acid, the library of sequences within a given loop will contain the target amino acid at all combinations of one to all positions within the loop at which the consensus amino acid has an occurrence frequency equal to or less than the given threshold frequency. If this threshold frequency is set at 100%, each position in the loop will be contain the target amino acid in at least one library member. The "library mutagenesis sequences" can be generated from the Tables and Figures disclosed herein using commercial vendors such as Geneart, or DNA2.0.

The term "library of natural-variant combinatorial sequences" refers to a library of sequences within a selected Fn3 loop and loop length which is expressed by a library of coding sequences that encode at each loop position, a conserved or selected semi-conserved consensus amino acid and, if the consensus amino acid has a frequency of occurrence equal to or less than a selected threshold frequency of at least 50%, other natural variant amino acids, including semi-conserved amino acids and variable amino acids whose occurrence rate is above a selected minimum threshold occurrence at that position, or their chemical equivalents. Thus, for each amino acid position in a selected loop and loop length, the library of natural variant combinatorial sequences will contain the consensus amino acid at that position plus other amino acid variants identified as having at least some minimum frequency at that position, e.g., at least 5-10% frequency, or chemically equivalent amino acids. In addition, natural variants may be substituted or dropped if the coding sequence for that amino acid produces a significant number of co-produced amino acids, via codon degeneracy.

The term "variability profile" or "VP" refers to the cataloguing of amino acids and their respective frequency rates of occurrence present at a particular loop position. The loop positions are derived from an aligned fibronectin dataset.

The term "amino acid" or "amino acid residue" typically refers to an amino acid having its art recognized definition such as an amino acid selected from the group consisting of: alanine (Ala, A); arginine (Arg, R); asparagine (Asn, N); aspartic acid (Asp, D); cysteine (Cys, C); glutamine (Gln, Q); glutamic acid (Glu, E); glycine (Gly, G); histidine (His, H); isoleucine (Ile, I): leucine (Leu, L); lysine (Lys, K); methionine (Met, M); phenylalanine (Phe, F); proline (Pro, P); serine (Ser, S); threonine (Thr, T); tryptophan (Trp, W); tyrosine (Tyr, Y); and valine (Val, V) although modified, synthetic, or rare amino acids may be used as desired.

The term "chemically equivalent amino acids" refers to amino acids that have similar steric, charge, and solubility properties. One common scheme groups amino acids in the following way: (1) glycine, having a hydrogen side chain; (2) alanine (Ala, A), valine (Val, V), leucine (Leu, L), and isoleucine (Iso, I), having hydrogen or an unsubstituted aliphatic side chain; (3) serine (Ser, S) and threonine (Thr, T) having an aliphatic side chain bearing a hydroxyl group; (4) aspartic (Asp, D) and glutamic acid (Glu, E), having a carboxyl containing side chain; (5) asparagine (Asn, N) and glutamine (Glu, Q), having an aliphatic side chain terminating in an amide group; (6) arginine (Arg, R) lysine (Lys, L) and histidine (His, H), having an aliphatic side chain terminating in a basic amino group; (7) cysteine (Cys, C) and methionine (Met, M), having a sulfur containing aliphatic side chain; (8) tyrosine (Tyr, Y) and phenylalanine (Phe, F), having an aromatic side chain; and (9) tryptophan (Trp, W), praline (Pro, P), and histidine (His, H), having a heterocyclic side chain.

The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides may be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety. Polynucleotide basis and alternative base pairs are given their usual abbreviations herein: Adenosine (A), Guanosine (G), Cytidine (C), Thymidine (T), Uridine (U), puRine (R=A/G), pyrimidine (Y=C/T or C/U), aMino (M=A/C), Keto (K=G/T or G/U), Strong (S=G/C), Weak (W=A/T or A/U), V (A or C or G, but not T), N or X, (any base).

The term "mutagenesis" refers to, unless otherwise specified, any art recognized technique for altering a polynucleotide or polypeptide sequence. Examples of mutagenesis include, but are not limited to, walk-through mutagenesis (WTM), natural-variant combinatorial mutagenesis, and beneficial natural-variant combinatorial mutagenesis, although other mutagenesis libraries may be employed, such as look-through mutagenesis (LTM), II. Overview of the Method and Libraries Artificial antibody scaffolds that bind specific ligands are becoming legitimate alternatives to antibodies. Antibodies have been useful as both diagnostic and therapeutic tools. However, obtaining specific antibodies recognizing certain targets have been difficult. Current antibody libraries are biased against certain antigen classes only after immunological exposure. Therefore it is frequently necessary to immunize a host animal with a particular antigen before recovery of specific antibodies can occur. Furthermore, antibodies are difficult and expensive to produce requiring special cell fermentation reactors and purification procedures.

The limitations of antibodies has spurred the development of alternative binding proteins based on immunoglobulin like folds or other protein topologies. These non-antibody scaffold share the general quality of having a structurally stable framework core that is tolerant to multiple substitutions in other parts of the protein.

The present invention provides a universal fibronectin bottom-side binding domains and a library of fibronectin bottom-side binding domains that use the bottom side loop regions (AB, CD, or EF). These bottom side Fn3 binding domains and libraries of bottom side Fn3 binding domains are more comprehensive and engineered to have artificial diversity in the target binding loops. By creating artificial diversity, the library size can be controlled so that they can be readily screened using, for example, high throughput methods to obtain new therapeutics. The universal fibronectin library with bottom side loop regions can be screened using positive physical clone selection by FACS, phage panning or selective ligand retention. These in vitro screens bypass the standard and tedious methodology inherent in generating an antibody hybridoma library and supernatant screening.

Furthermore, the universal fibronectin library with the bottom side loop regions (AB, CD, or EF) has the potential to recognize any target as the constituent amino acids in the target binding loop are created by in vitro diversity techniques. This produces the significant advantages of the library controlling diversity size and the capacity to recognize self antigens. Still further, the fibronectin bottom-side binding domain library with the bottom side loop regions (AB, CD, or EF) can be propagated and re-screened to discover additional fibronectin binding modules against other desired targets.

Fibronectin Review: (Fn)

Fibronectin Type III (Fn3) proteins refer to a group of proteins composed of momomeric subunits having Fibronectin Type III (Fn3) structure or motif made up of seven β-strands with three connecting loops. β-strands A, B, and E form one half β-sandwich and β-strands C, D, F, and G form the other half (see FIG. 1), and having molecular weights of about 94 amino acids and molecular weights of about 10 Kda. The overall fold of the Fn3 domain is closely related to that of the immunoglobulin domains, and the three loops near the N-terminus of Fn3, named BC, DE, and FG ncan be considered structurally analogous to the antibody variable heavy (VH) domain complementarity-determining regions, CDR1, CDR2, and CDR3, respectively. The bottom loops of Fn3 have typically been thought to confer structural stability rather than being used for binding targets. However, the methods of the invention demonstrate that the bottom loops can indeed be used for binding targets and for generating libraries of Fn3 binding molecules that use the top loops, the bottom loops or any combination of the top and bottom loops for binding.

The amino acid sequence of fibronectin reveals three types of internally homologous repeats or modules separated by (usually) short connecting sequences. There are 12 type I, 2 type II and 16 type III modules, and referred to as Fn I, FnII and FnIII respectively. Each Fn module constitutes an independently folded unit, often referred to as a domain. Within fibronectin itself, there are sixteen Fn3 domains and have remarkably similar tertiary structures. While Fn3 conformation are highly conserved, the similarity between different modules of the same type within a given fibronectin protein is quite low typically less than 20%.

Figure 1:
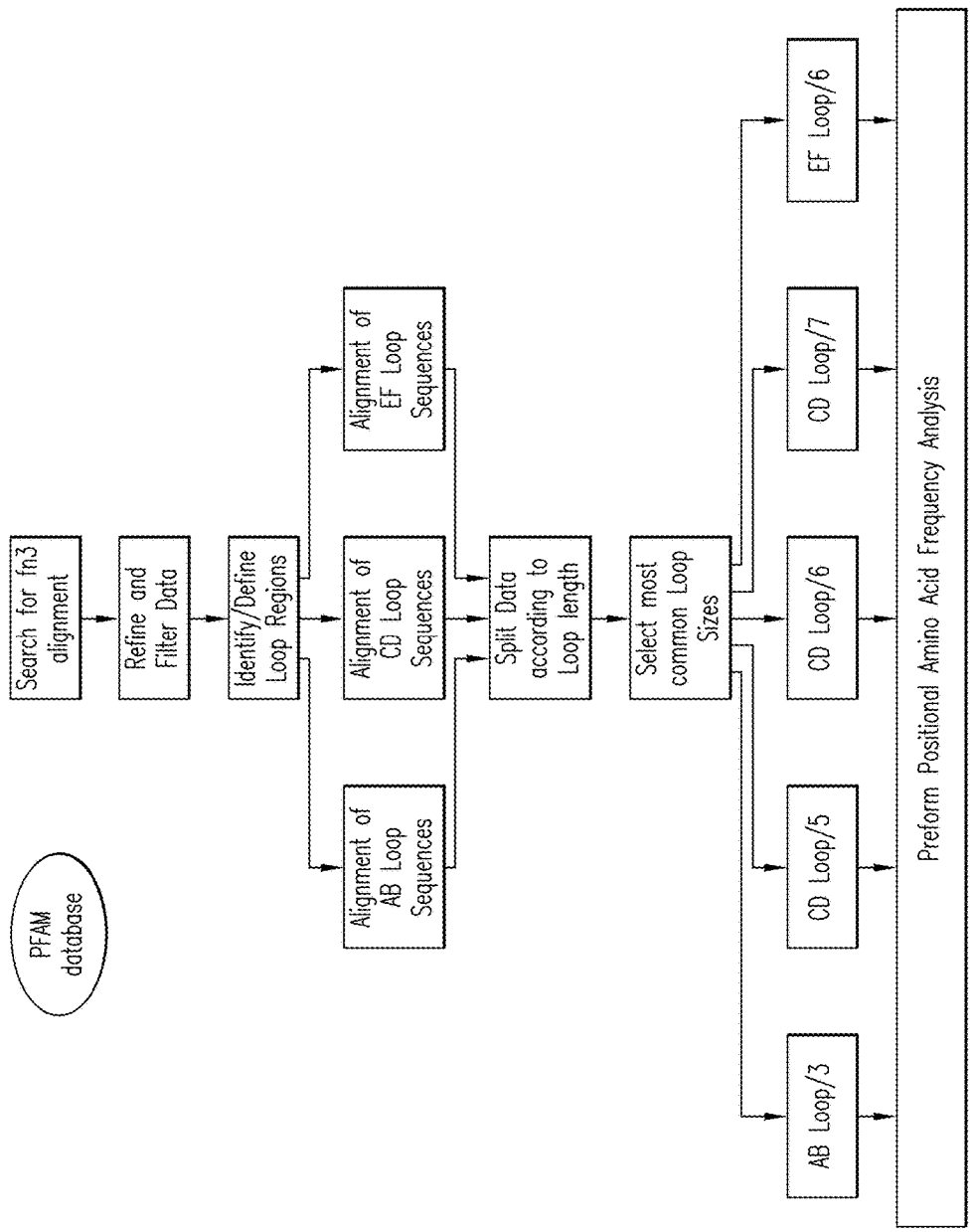
FIG. 1 is a schematic diagram illustrating the method for constructing a fibronectin bottom-side binding domain libraries using computer assisted genetic database biomining and delineation of beta-scaffold and loop structures.

Identifying and Selecting Fibronectin Scaffold and Loop Components Using Bioinformatics The first step in building a universal fibronectin library of the invention is selecting sequences that meet certain predetermined criteria. PFAM, ProSite and similar databases were searched for sequences containing Fn3 domains (FIG. 1). These electronic databases contain catalogued expressed fibronectin and fibronectin-like protein sequences and can be queried for those Fn3 modules and similar sequences (e.g., using the BLAST search algorithm). The Fn3 module sequences can then be grouped to predefined criteria such as module subclasses, sequence similarity or originating organism(s). The framework sequence selection can also be performed for scaffold proteins such as Fn I, Fn II or ankyrin and other proteins, such as SCALPs, SmALPs, NANOBODIES, and the like.

Candidate Fn3 β-strand scaffold framework sequences are then delineated whereupon the intervening loop regions and constituent amino acids are then identified. This then determines the length of the existing loops, the amino acid profiles for each loop length and, hence the physical size and amino acid diversity that can be accommodated within these frameworks. Once the loop are identified, sequences within each loop are aligned, and the aligned sequences are then split into groups according to loop length. The distribution of loop lengths for the AB, CD, and EF loops were identified. Using this information, the most common loop sizes are selected. In a general embodiment of the invention, the selected loop lengths are AB/3, CD/5, CD/6, CD/7, and EF/6, DE/6. For each β-strand, one can determine the preferred loop acceptor sites in the frameworks based on both comparative structural and sequence analysis. For example, one can use the structural overlay comparison of the overall loop and (3 strand scaffolds between the fibronectin $^{10}$Fn3, $^{14}$Fn3 or any of the other known Fn3 domains. In identifying precise loop positions, the above step greatly minimizes necessary diversity loop mutations that would not result in functional ligand binding specificity.

Once loop lengths are selected, a positional amino acid frequency analysis is performed at each loop position, to determine the frequency of occurrence, in a set of native Fn3 modules. This method includes a frequency analysis and the generation of the corresponding variability profiles (VP) of existing loop sequences (See Examples and FIGS. 3-10). High frequency (e.g. >50%) positions are considered conserved or fixed. Moderately high frequency or "semi-conserved" amino acids or (when 2 or 3 are combined account for >40%) are chosen as "wildtype" at other positions. These wildtype amino acids are then systematically altered using, mutagenesis, e.g. walk-through mutagenesis, to generate the universal loop library. "Variable" positions are those where typically, no one amino acid accounts for more than 20% of the represented set.

The choice of candidate frameworks based on the criteria of the invention dictates both the loop sizes to be introduced and the initial amino acid sequence diversity.

A loop variability profile analysis of the Fn3 databases allows identification of loop amino acid residue positions that fall within three categories, e.g., 1) positions that should be conserved or "fixed," and 2) semi-conserved and/or 3) variable positions that are suitable for diversity generation. A variability profile analysis is performed and a threshold frequency is used to identify the most favorable sequences to be used in designating the overall loop diversity.

The conserved or a selected semi-conserved sequence (typically the most frequent amino acid in the semi-conserved residues) is considered the "wild type" or "consensus" residue in the loop sequence. This "consensus" or "frequency" approach identifies those particular amino acids under high selective pressure that occurs most frequently at a particular position.

Accordingly, these residue positions are typically fixed, with diversity being introduced into remaining amino acid positions (taking into account the identified preference for certain amino acids to be present at these positions). The threshold for occurrence frequency at which amino acid variation will be introduced can vary between selected levels as low as 40%, preferably 50% to as high as 100%. At the 100% threshold frequency, mutagenesis of amino acids can be introduced at all positions of the loop, and the only constraints on natural-variant amino acids will be the total number of variants and whether chemical equivalents are available.

When designing the diversity for any of the above-mentioned loops, modified amino acid residues, for example, residues outside the traditional 20 amino acids used in most polypeptides, e.g., homocysteine, can be incorporated into the loops as desired. This is carried out using art recognized techniques which typically introduce stop codons into the polynucleotide where the modified amino acid residue is desired. The technique then provides a modified tRNA linked to the modified amino acid to be incorporated (a so-called suppressor tRNA of, e.g., the stop codon amber, opal, or ochre) into the polypeptide (see, e.g., Köhrer et al., Import of amber and ochre suppressors tRNAs into mammalian cells: A general approach to site-specific insertion of amino acid analogues into proteins, PNAS, 98, 14310-14315 (2001)).

The bioinformatic analysis focuses on Fn3 modules genes for descriptive purposes, but it will be understood that genes for other Fn modules and other scaffold protein are similarly evaluated. In one embodiment, the bioinformatics analysis can be applied for single chain antibody-like proteins (SCALPs), nanobodies, and the like.

Computer-Assisted Universal Fibronectin Library Construction

The universal fibronectin bottom loop libraries of the invention and their construction is conducted with the benefit of sequence and structural information such that the potential for generating improved fibronectin binding domains is increased. Structural molecular replacement modeling information can also be used to guide the selection of amino acid diversity to be introduced into the defined loop regions. Still further, actual results obtained with the fibronectin binding domains of the invention can guide the selection (or exclusion), e.g., affinity maturation, of subsequent fibronectin binding domains to be made and screened in an iterative manner.

In one embodiment, in silico modeling is used to eliminate the production of any fibronectin binding domains predicted to have poor or undesired structure and/or function. In this way, the number of fibronectin binding domains to be produced can be sharply reduced thereby increasing signal-to-noise in subsequent screening assays. In another particular embodiment, the in silico modeling is continually updated with additional modeling information, from any relevant source, e.g., from gene and protein sequence and three-dimensional databases and/or results from previously tested fibronectin binding domains, so that the in silico database becomes more precise in its predictive ability (FIG. 1).

In yet another embodiment, the in silico database is provided with the assay results, e.g., binding affinity/avidity of previously tested fibronectin binding domains and categorizes the fibronectin binding domains, based on the assay criterion or criteria, as responders or nonresponders, e.g., as fibronectin binding domain molecules that bind well or not so well. In this way, the affinity maturation of the invention can equate a range of functional responses with particular sequence and structural information and use such information to guide the production of future fibronectin binding domains to be tested. The method is especially suitable for screening fibronectin binding domains for a particular binding affinity to a target ligand using, e.g., a Biacore assay.

Accordingly, mutagenesis of noncontiguous residues within a loop region can be desirable if it is known, e.g., through in silico modeling, that certain residues in the region will not participate in the desired function. The coordinate structure and spatial interrelationship between the defined regions, e.g., the functional amino acid residues in the defined regions of the fibronectin binding domain, e.g., the diversity that has been introduced, can be considered and modeled. Such modeling criteria include, e.g., amino acid residue side group chemistry, atom distances, crystallography data, etc. Accordingly, the number fibronectin binding domains to be produced can be intelligently minimized.

In one embodiment, one or more of the above steps are computer-assisted. In a particular embodiment, the computer assisted step comprises, e.g., mining the NCBI, Genbank, PFAM, and ProSite databases and, optionally, cross-referencing the results against PDB structural database, whereby certain criteria of the invention are determined and used to design the desired loop diversity (FIG. 1). The method is also amenable to being carried out, in part or in whole, by a device, e.g., a computer driven device. For example, database mining fibronectin module sequence selection, diversity design, oligonucleotide synthesis, PCR-mediated assembly of the foregoing, and expression and selection of candidate fibronectin binding domains that bind a given target, can be carried out in part or entirely, by interlaced devices. In addition, instructions for carrying out the method, in part or in whole, can be conferred to a medium suitable for use in an electronic device for carrying out the instructions. In sum, the methods of the invention are amendable to a high throughput approach comprising software (e.g., computer-readable instructions) and hardware (e.g., computers, robotics, and chips).

Universal Mutagenesis Libraries

The present invention pertains to a mutagenesis library of fibronectin Type 3 domain polypeptides useful in screening for the presence of one or more polypeptides having a selected binding or enzymatic activity. The library polypeptides include (a) regions A, AB, B, C, CD, D, E, EF, F, and G having wildtype amino acid sequences of a selected native fibronectin Type 3 polypeptide or polypeptides, and (b) loop regions AB, CD, and EF having one or more selected lengths. At least one selected loop region of a selected length contains a library of sequences encoded by a library of coding sequences that encode, at each loop position, a conserved or selected semi-conserved consensus amino acid and, if the consensus amino acid has a occurrence frequency equal to or less than a selected threshold frequency of at least 50%, a single common target amino acid and any co-produced amino acids (amino acids produced by the coding sequences at a given position as a result of codon degeneracy).

In constructing a library within a given loop of a given loop length, the variability profile is used to define a sequence of fixed and "variable" positions, i.e., positions at which a target amino acid can be introduced. The number of fixed positions will depend on the selected threshold frequency for the consensus amino acid at each position.

Once the loop sequences are selected, a library of coding-sequence oligonucleotides encoding all of the identified sequences is constructed, making codon substitutions as shown that are effective to preserve the existing consensus amino acid, but also encode the selected target amino acid, and any other co-product amino acids encoded by degenerate codons.

The library of coding sequences for the loops is added to the framework sequences, to construct the library of coding sequences for the polypeptide libraries. The library of polypeptides may be encoded by an expression library format that includes a ribosome display library, a polysome display library, a phage display library, a bacterial expression library, or a yeast display library.

The libraries may be used in a method of identifying a polypeptide having a desired binding affinity, in which the natural-variant combinatorial library are screened to select for an fibronectin binding domain having a desired binding affinity.

In another embodiment, universal natural-variant combinatorial mutagenesis libraries can be generated. The invention includes a natural-variant combinatorial library of fibronectin Type 3 domain polypeptides useful in screening for the presence of one or more polypeptides having a selected binding or enzymatic activity. The library polypeptides include (a) regions A, AB, B, C, CD, D, E, EF, F, and G having wildtype amino acid sequences of a selected native fibronectin Type 3 polypeptide or polypeptides, and (b) loop regions AB, CD, and EF having selected lengths. At least one selected loop region of a selected length contains a library of natural-variant combinatorial sequences expressed by a library of coding sequences that encode at each loop position, a conserved or selected semi-conserved consensus amino acid and, if the consensus amino acid has a frequency of occurrence equal to or less than a selected threshold frequency of at least 50%, other natural variant amino acids, including semi-conserved amino acids and variable amino acids whose occurrence rate is above a selected minimum threshold occurrence at that position, or their chemical equivalents.

In constructing a natural-variant combinatorial library for a given loop and loop length, the variability profile is used to define a sequence of fixed and "variable" positions, i.e., positions at which amino acid variations can be introduced. In the libraries, the number of fixed positions will depend on the selected threshold frequency for the consensus amino acid at each position. If, for example, the selected frequency threshold was set at about 60%, the conserved or semi-conserved residues and natural-variant substitutions would not be made at these positions. Conversely, if the threshold frequency is set at 100%, all positions would be considered open to variation, recognizing that a single amino acid with a frequency of 100% at a loop position would not be substituted, and a position that had one very dominant amino acid, e.g., with a frequency of 90%, might be substituted only if the low-frequency variant(s) were chemically dissimilar to the dominant amino acid.

From the amino acid profile for a given loop and loop length, and knowing which of the positions will be held fixed and which will be admit variations, the amino acid substitutions at each variable position can be selected. In general, the number of variations that are selected (including co-produced amino acids) will depend on the number of variable substitution positions in the loop and the average number of variations per substituted loop position. Of course, if natural-variant substitutions are introduced into a single loop only, many more variations per position can be accommodated.

The particular natural variant amino acids that are selected for each position will generally include the amino acids having the highest frequencies, while limited the number of co-produced amino acids, and secondarily, preserving chemical diversity at each site. Once the natural-variant loop sequences are selected, a library of coding-sequence oligonucleotides encoding all of the identified natural-variant sequences is constructed, making codon substitutions that are effective to preserve the existing consensus amino acid, and encode the selected variant amino acids, including variants encoded encoded by degenerate codons.

The library of coding sequences for the natural-variants loops is added to the framework sequences, to construct the library of coding sequences for the natural-variant polypeptide libraries. In one embodiment, the coding library includes coding sequences for a pair of AB/CD, AB/EF or CD/EF loops, where each loop in the pair has one selected length. After selecting high-affinity binding (or enzymatic) polypeptides from this library, a second "beneficial" library can be constructed that includes the beneficial mutations contained in one or both of original two-loop natural-variation library, and natural-variant amino acids in the third loop, i.e., the previously fixed-sequence loop. In another embodiment, the coding library includes coding sequences for all three loops, AB, CD and EF.

The library of polypeptides may be encoded by an expression library that has the format of a ribosome display library, a polysome display library, a phage display library, a bacterial expression library, or a yeast display library.

Synthesizing Universal Fibronectin Bottom-Side Binding Domain Libraries

In one embodiment, the universal fibronectin bottom-side binding domains of the invention are generated for screening by synthesizing individual oligonucleotides that encode the defined region of the polypeptide and have no more than one codon for the predetermined amino acid. This is accomplished by incorporating, at each codon position within the oligonucleotide either the codon required for synthesis of the wild-type polypeptide or a codon for the predetermined amino acid and is referred to as look-through mutagenesis (LTM) (see, e.g., U.S. Patent Publication No. 20050136428).

In another embodiment, when diversity at multiple amino acid positions is required, walk-through mutagenesis (WTM) can be used (see e.g., U.S. Pat. Nos. 6,649,340; 5,830,650; and 5,798,208; and U.S. Patent Publication No. 20050136428. In another embodiment, diversity can be created using the methods available from commercial vendors such as DNA2.0 and Geneart by providing information about the loop lengths of the AB, CD, and EF loops, the positional distribution of amino acids at each position of the loop, and the top 7 amino acid abundance at each position of the loop.

In addition, the methods of the invention also provide other libraries referred to as the "N+/− libraries." These N+/− libraries are constructed with variations in bottom loops, AB, CD, and EF, the top loops, BC, DE, FG, or any combination of top and bottom loops. For "N+/− libraries," N is the most predominant amino acid at a particular position and amino acids upstream or downstream are designated +N or —N, respectively. For example, N+3 is an amino acid 3 positions upstream of N, while N−3 is an amino acid 3 positions downstream of N in a 3D structure of Fn3. Likewise, N+2 and N+1 are amino acids at positions 2 and 1 upstream of N, respectively, while N−2 and N−1 are amino acids at positions 2 and 1 downstream of N, respectively. By altering, N from the most predominantly abundant amino acid to a less abundant amino acid, the effect of that modification can be assessed on the abundance of amino acids at 1, 2, or 3 positions away from N. In designing such a library, the frequency and abundance of amino acids surrounding the fixed N position are determined. These differences can be used to generate universal fibronectin bottom-side binding domain libraries, top-side binding domain libraries, or a combination of both bottom-side and top-side binding domain libraries.

For illustrative purposes only, the consensus sequence in the CD/5 loop as shown in FIGS. 6AB, is GDGQP at loop positions 1, 2, 3, 4, and 5 (SEQ ID NO.: 34), with G being the predominant amino acid. Using the N+/− theory, if G in loop position 3 is fixed as it is the predominant amino acid (N), then the structural and microenvironmental effect of G on loop position 1 (N−2), loop position 2 (N−1), loop position 4 (N+1), and loop position 5 (N+2) is determined. The amino acid frequency of each position N−2, N−1, N+1, N+2 in the context of a fixed G at position N is calculated. Then, if G at loop position 3 is changed to S, the effect of S on positions N−2, N−1, N+1, N+2 (i.e., loop positions 1, 2, and 4, 5,) is determined, and so forth. After all possible combinations are calculated the information yielded is an amino acid distribution (N−2, N−1, N, N+1, N+2) of a given position N within a predetermined loop region in the context of a specific amino acid at this position N. This information can then be used to generate a library.

In another illustration, the concensus sequence of EF/6 as shown in FIGS. 10AB, is GLKPGT at loop positions 1, 2, 3, 4, 5, and 6, respectively of the EF loop. Using the N+/− theory, if L in position 2 is kept fixed as it is the predominant amino acid (N), then the structural and local microenvironmental effect on G at position 1 (N−1), K at position 3 (N+1), P at position 4 (N+2), G at position 5 (N+3), and T at position 6 (N+4), is determined. Moreover, if L at position 2 is changed to V, then the effect of this change on positions N−1, N+1, N+2, N+3 and N+4 (i.e., loop positions 1, 3, 4, 5, and 6) is determined.

The mixture of oligonucleotides for generation of the library can be synthesized readily by known methods for DNA synthesis. The preferred method involves use of solid phase beta-cyanoethyl phosphoramidite chemistry (e.g., see U.S. Pat. No. 4,725,677). For convenience, an instrument for automated DNA synthesis can be used containing specified reagent vessels of nucleotides. The polynucleotides may also be synthesized to contain restriction sites or primer hybridization sites to facilitate the introduction or assembly of the polynucleotides representing, e.g., a defined region, into a larger gene context.

The synthesized polynucleotides can be inserted into a larger gene context, e.g., a single scaffold domain using standard genetic engineering techniques. For example, the polynucleotides can be made to contain flanking recognition sites for restriction enzymes (e.g., see U.S. Pat. No. 4,888, 286). The recognition sites can be designed to correspond to recognition sites that either exist naturally or are introduced in the gene proximate to the DNA encoding the region. After conversion into double stranded form, the polynucleotides are ligated into the gene or gene vector by standard techniques. By means of an appropriate vector (including, e.g., phage vectors, plasmids) the genes can be introduced into a cell-free extract, phage, prokaryotic cell, or eukaryotic cell suitable for expression of the fibronectin binding domain molecules.

When partially overlapping polynucleotides are used in the gene assembly, a set of degenerate nucleotides can also be directly incorporated in place of one of the polynucleotides. The appropriate complementary strand is synthesized during the extension reaction from a partially complementary polynucleotide from the other strand by enzymatic extension with a polymerase. Incorporation of the degenerate polynucleotides at the stage of synthesis also simplifies cloning where more than one domain or defined region of a gene is mutagenized or engineered to have diversity.

In another approach, the fibronectin binding domain is present on a single stranded plasmid. For example, the gene can be cloned into a phage vector or a vector with a filamentous phage origin of replication that allows propagation of single-stranded molecules with the use of a helper phage. The single-stranded template can be annealed with a set of degenerate polynucleotides representing the desired mutations and elongated and ligated, thus incorporating each analog strand into a population of molecules that can be introduced into an appropriate host (see, e.g., Sayers, J. R. et al., Nucleic Acids Res. 16: 791-802 (1988)). This approach can circumvent multiple cloning steps where multiple domains are selected for mutagenesis.

Polymerase chain reaction (PCR) methodology can also be used to incorporate polynucleotides into a gene, for example, loop diversity into β-strand framework regions. For example, the polynucleotides themselves can be used as primers for extension. In this approach, polynucleotides encoding the mutagenic cassettes corresponding to the defined region (or portion thereof) are complementary to each other, at least in part, and can be extended to form a large gene cassette (e.g., a fibronectin binding domain) using a polymerase, e.g., using PCR amplification.

The size of the library will vary depending upon the loop length and the amount of sequence diversity which needs to be represented using mutagenesis methods. For example, the library is designed to contain less than $10^{15}$, $10^{14}$, $10^{13}$, $10^{12}$, $10^{11}$, $10^{10}$, $10^{9}$, $10^{8}$, $10^{7}$, and $10^{6}$ fibronectin binding domain.

The description above has centered on representing fibronectin binding domain diversity by altering the polynucleotide that encodes the corresponding polypeptide. It is understood, however, that the scope of the invention also encompasses methods of representing the fibronectin binding domain diversity disclosed herein by direct synthesis of the desired polypeptide regions using protein chemistry. In carrying out this approach, the resultant polypeptides still incorporate the features of the invention except that the use of a polynucleotide intermediate can be eliminated.

For the libraries described above, whether in the form of polynucleotides and/or corresponding polypeptides, it is understood that the libraries may be also attached to a solid support, such as a microchip, and preferably arrayed, using art recognized techniques.

The method of this invention is especially useful for modifying candidate fibronectin binding domain molecules by way of affinity maturation. Alterations can be introduced into the loops and/or into the β-strand framework (constant) region of an fibronectin binding domain. Modification of the loop regions can produce fibronectin binding domains with better ligand binding properties, and, if desired, catalytic properties. Modification of the β-strand framework region can also lead to the improvement of chemo-physical properties, such as solubility or stability, which are especially useful, for example, in commercial production, bioavailabilty, and affinity for the ligand. Typically, the mutagenesis will target the loop region(s) of the fibronectin binding domain, i.e., the structure responsible for ligand-binding activity which can be made up of the three loop regions. In a preferred embodiment, an identified candidate binding molecule is subjected to affinity maturation to increase the affinity/avidity of the binding molecule to a target ligand.

Expression and Screening Systems

Libraries of polynucleotides generated by any of the above techniques or other suitable techniques can be expressed and screened to identify fibronectin binding domain molecules having desired structure and/or activity. Expression of the fibronectin binding domain molecules can be carried out using cell-free extracts (and e.g., ribosome display), phage display, prokaryotic cells, or eukaryotic cells (e.g., yeast display).

In one embodiment, the polynucleotides are engineered to serve as templates that can be expressed in a cell free extract. Vectors and extracts as described, for example in U.S. Pat. Nos. 5,324,637; 5,492,817; 5,665,563, can be used and many are commercially available. Ribosome display and other cell-free techniques for linking a polynucleotide (i.e., a genotype) to a polypeptide (i.e., a phenotype) can be used, e.g., Profusion™ (see, e.g., U.S. Pat. Nos. 6,348,315; 6,261,804; 6,258,558; and 6,214,553).

Alternatively, the polynucleotides of the invention can be expressed in a convenient E. coli expression system, such as that described by Pluckthun and Skerra. (Pluckthun, A. and Skerra, A., Meth. Enzymol. 178: 476-515 (1989); Skerra, A. et al., Biotechnology 9: 273-278 (1991)). The mutant proteins can be expressed for secretion in the medium and/or in the cytoplasm of the bacteria, as described by M. Better and A. Horwitz, Meth. Enzymol. 178: 476 (1989). In one embodiment, the fibronectin binding domain are attached to the 3' end of a sequence encoding a signal sequence, such as the ompA, phoA or pelB signal sequence (Lei, S. P. et al., J. Bacteriol. 169: 4379 (1987)). These gene fusions are assembled in a dicistronic construct, so that they can be expressed from a single vector, and secreted into the periplasmic space of E. coli where they will refold and can be recovered in active form. (Skerra, A. et al., Biotechnology 9: 273-278 (1991)).

In another embodiment, the fibronectin binding domain sequences are expressed on the membrane surface of a prokaryote, e.g., E. coli, using a secretion signal and lipidation moiety as described, e.g., in US20040072740A1; US20030100023A1; and US20030036092A1.

In still another embodiment, the polynucleotides can be expressed in eukaryotic cells such as yeast using, for example, yeast display as described, e.g., in U.S. Pat. Nos. 6,423,538; 6,331,391; and 6,300,065. In this approach, the fibronectin binding domain molecules of the library are fused to a polypeptide that is expressed and displayed on the surface of the yeast.

Higher eukaryotic cells for expression of the fibronectin binding domain molecules of the invention can also be used, such as mammalian cells, for example myeloma cells (e.g., NS/0 cells), hybridoma cells, or Chinese hamster ovary (CHO) cells. Typically, the fibronectin binding domain molecules when expressed in mammalian cells are designed to be expressed into the culture medium, or expressed on the surface of such a cell. The fibronectin binding domain can be produced, for example, as single individual module or as multimeric chains comprising dimers, trimers, that can be composed of the same module or of different module types. (10Fn3-10Fn3: homodimer, 10Fn3-8Fn3: heterodimer).

The screening of the expressed fibronectin binding domain (or fibronectin binding domain produced by direct synthesis) can be done by any appropriate means. For example, binding activity can be evaluated by standard immunoassay and/or affinity chromatography. Screening of the fibronectin binding domain of the invention for catalytic function, e.g., proteolytic function can be accomplished using a standard hemoglobin plaque assay as described, for example, in U.S. Pat. No. 5,798,208. Determining the ability of candidate fibronectin binding domain to bind therapeutic targets can be assayed in vitro using, e.g., a Biacore instrument, which measures binding rates of a fibronectin binding domain to a given target or ligand. In vivo assays can be conducted using any of a number of animal models and then subsequently tested, as appropriate, in humans.

Analysis and Screening of Fn3 Libraries for Catalytic Function.

Fn3 libraries can also be used to screen for Fn3 proteins that possess catalytic activity. The study of proteins has revealed that certain amino acids play a crucial role in their structure and function. For example, it appears that only a discrete number of amino acids participate in the catalytic event of an enzyme. Serine proteases are a family of enzymes present in virtually all organisms, which have evolved a structurally similar catalytic site characterized by the combined presence of serine, histidine and aspartic acid. These amino acids form a catalytic triad which, possibly along with other determinants, stabilizes the transition state of the substrate. The functional role of this catalytic triad has been confirmed by individual and by multiple substitutions of serine, histidine and aspartic acid by site-directed mutagenesis of serine proteases and the importance of the interplay between these amino acid residues in catalysis is now well established.

Similarly, a large number of other types of enzymes are characterized by the peculiar conformation of their catalytic site and the presence of certain kinds of amino acid residues in the site that are primarily responsible for the catalytic event. For an extensive review, see Enzyme Structure and Mechanism, 1985, by A. Fersht, Freeman Ed., New York.

Though it is clear that certain amino acids are critical to the mechanism of catalysis, it is difficult, if not impossible, to predict which position (or positions) an amino acid must occupy to produce a functional site such as a catalytic site. Unfortunately, the complex spatial configuration of amino acid side chains in proteins and the interrelationship of different side chains in the catalytic pocket of enzymes are insufficiently understood to allow for such predictions. Selective site-directed mutagenesis and saturation mutagenesis are of limited utility for the study of protein structure and function in view of the enormous number of possible variations in complex proteins.

Protein libraries generated by any of the above techniques or other suitable techniques can be screened to identify variants of desired structure or activity.

By comparing the properties of a wild-type protein and the variants generated, it is possible to identify individual amino acids or domains of amino acids that confer binding and/or catalytic activity. Usually, the region studied will be a functional domain of the protein such as a binding domain. For example, the region can be the AB, CD and EF loop binding regions of Fn3 domain. The screening can be done by any appropriate means. For example, catalytic activity can be ascertained by suitable assays for substrate conversion and binding activity can be evaluated by standard immunoassay and/or affinity chromatography.

From the chemical properties of the side chains, it appears that only a selected number of natural amino acids preferentially participate in a catalytic event. These amino acids belong to the group of polar and neutral amino acids such as Ser, Thr, Asn, Gln, Tyr, and Cys, the group of charged amino acids, Asp and Glu, Lys and Arg, and especially the amino acid His. Typical polar and neutral side chains are those of Cys, Ser, Thr, Asn, Gln and Tyr. Gly is also considered to be a borderline member of this group. Ser and Thr play an important role in forming hydrogen-bonds. Thr has an additional asymmetry at the beta carbon, therefore only one of the stereoisomers is used. The acid amide Gln and Asn can also form hydrogen bonds, the amido groups functioning as hydrogen donors and the carbonyl groups functioning as acceptors. Gln has one more $CH_2$ group than Asn which renders the polar group more flexible and reduces its interaction with the main chain. Tyr has a very polar hydroxyl group (phenolic OH) that can dissociate at high pH values. Tyr behaves somewhat like a charged side chain; its hydrogen bonds are rather strong.

Histidine (His) has a heterocyclic aromatic side chain with a pK value of 6.0. In the physiological pH range, its imidazole ring can be either uncharged or charged, after taking up a hydrogen ion from the solution. Since these two states are readily available, His is quite suitable for catalyzing chemical reactions. It is found in most of the active centers of enzymes.

Asp and Glu are negatively charged at physiological pH. Because of their short side chain, the carboxyl group of Asp is rather rigid with respect to the main chain. This may be the reason why the carboxyl group in many catalytic sites is provided by Asp and not by Glu. Charged acids are generally found at the surface of a protein.

Therefore, several different regions or loops of a Fn3 protein domain can be mutagenized simultaneously. This enables the evaluation of amino acid substitutions in conformationally related regions such as the regions which, upon folding of the protein, are associated to make up a functional site such as the catalytic site of an enzyme or the binding site of an antibody. This method provides a way to create modified or completely new catalytic sites. The three loop regions of Fn3, which can be engineered to confer target ligand binding, can be mutagenized simultaneously, or separately within the AB, CD and EF loops to assay for contributing catalytic functions at this binding site. Therefore, the introduction of additional "catalytically important" amino acids into a ligand binding region of a protein may result in de novo catalytic activity toward the same target ligand.

Hence, new structures can be built on the natural "scaffold" of an existing protein by mutating only relevant regions by the method of this invention. The method of this invention is suited to the design of de novo catalytic binding proteins as compared to the isolation of naturally occurring catalytic antibodies. Presently, catalytic antibodies can be prepared by an adaptation of standard somatic cell fusion techniques. In this process, an animal is immunized with an antigen that resembles the transition state of the desired substrate to induce production of an antibody that binds the transition state and catalyzes the reaction. Antibody-producing cells are harvested from the animal and fused with an immortalizing cell to produce hybrid cells. These cells are then screened for secretion of an antibody that catalyzes the reaction. This process is dependent upon the availability of analogues of the transition state of a substrate. The process may be limited because such analogues are likely to be difficult to identify or synthesize in most cases.

The method of this invention can be used to produce many different enzymes or catalytic antibodies, including oxidoreductases, transferases, hydrolases, lyases, isomerases and ligases. Among these classes, of particular importance will be the production of improved proteases, carbohydrases, lipases, dioxygenases and peroxidases. These and other enzymes that can be prepared by the method of this invention have important commercial applications for enzymatic conversions in health care, cosmetics, foods, brewing, detergents, environment (e.g., wastewater treatment), agriculture, tanning, textiles, and other chemical processes. These include, but are not limited to, diagnostic and therapeutic applications, conversions of fats, carbohydrates and protein, degradation of organic pollutants and synthesis of chemicals. For example, therapeutically effective proteases with fibrinolytic activity, or activity against viral structures necessary for infectivity, such as viral coat proteins, could be engineered. Such proteases could be useful anti-thrombotic agents or anti-viral agents against viruses such as AIDS, rhinoviruses, influenza, or hepatitis. In the case of oxygenases (e.g., dioxygenases), a class of enzymes requiring a co-factor for oxidation of aromatic rings and other double bonds, industrial applications in biopulping processes, conversion of biomass into fuels or other chemicals, conversion of waste water contaminants, bioprocessing of coal, and detoxification of hazardous organic compounds are possible applications of novel proteins.

Methods for Generating Universal Fibronectin Bottom-Side Binding Domain Libraries In general, the practice of the present invention employs, unless otherwise indicated, conventional techniques of chemistry, molecular biology, recombinant DNA technology, PCR technology, immunology (especially, e.g., antibody technology), expression systems (e.g., cell-free expression, phage display, ribosome display, and Profusion™), and any necessary cell culture that are within the skill of the art and are explained in the literature. See, e.g., Sambrook, Fritsch and Maniatis, Molecular Cloning: Cold Spring Harbor Laboratory Press (1989); DNA Cloning, Vols. 1 and 2, (D. N. Glover, Ed. 1985); Oligonucleotide Synthesis (M. J. Gait, Ed. 1984); PCR Handbook Current Protocols in Nucleic Acid Chemistry, Beaucage, Ed. John Wiley & Sons (1999) (Editor); Oxford Handbook of Nucleic Acid Structure, Neidle, Ed., Oxford Univ Press (1999); PCR Protocols: A Guide to Methods and Applications, Innis et al., Academic Press (1990); PCR Essential Techniques: Essential Techniques, Burke, Ed., John Wiley & Son Ltd (1996); The PCR Technique: RT-PCR, Siebert, Ed., Eaton Pub. Co. (1998); Current Protocols in Molecular Biology, eds. Ausubel et al., John Wiley & Sons (1992); Large-Scale Mammalian Cell Culture Technology, Lubiniecki, A., Ed., Marcel Dekker, Pub., (1990). Phage Display: A Laboratory Manual, C. Barbas (Ed.), CSHL Press, (2001); Antibody Phage Display, P O'Brien (Ed.), Humana Press (2001); Border et al., Yeast surface display for screening combinatorial polypeptide libraries, Nature Biotechnology, 15(6):553-7 (1997); Border et al., Yeast surface display for directed evolution of protein expression, affinity, and stability, Methods Enzymol., 328: 430-44 (2000); ribosome display as described by Pluckthun et al. in U.S. Pat. No. 6,348,315, and Profusion™ as described by Szostak et al. in U.S. Pat. Nos. 6,258,558; 6,261,804; and 6,214,553, and bacterial periplasmic expression as described in US20040058403A1.

Further details regarding fibronectin and Fn3 sequence classification, identification, and analysis may be found, e.g., PFAM. A program to screen aligned nucleotide and amino acid sequences, Methods Mol. Biol. 1995; 51:1-15. and Wu et al. Clustering of highly homologous sequences to reduce the size of large protein databases. Bioinformatics. 2001 March; 17(3):282-3; Databases and search and analysis programs include the PFAM database at the Sanger Institute (pfam.sanger.ac.uk); the ExPASy PROSITE database (www.expasv.ch/prosite/); SBASE web (hydra.icgeb.trieste.it/sbase/); BLAST (www.ncbi.nlm.nih.gov/BLAST/); CD-HIT (bioinformatics.ljcrf.edu/cd-hi/); EMBOSS (www.hqmp.mrc.ac.uk/Software/EMBOSS/); PHYLIP (evolution.genetics.washington.edu/phylip.html); and FASTA (fasta.bioch.virginia.edu).

Yeast:

The fibronectin bottom-side binding domain library is transfected into the recipient bacterial/yeast hosts using standard techniques as described in the Examples. Yeast can readily accommodate library sizes up to $10^7$, with $10^3$-$10^5$ copies of each FnII fusion protein being displayed on each cell surface. Yeast cells are easily screened and separated using flow cytometry and fluorescence-activated cell sorting (FACS) or magnetic beads. The yeast eukaryotic secretion system and glycosylation pathways of yeast also allows Fn3 type molecules to be displayed with N and O linked sugars on the cell surface. Details of yeast display are outlined in the Examples section.

In another embodiment, the yeast display system utilizes the a-agglutinin yeast adhesion receptor to display proteins on the cell surface. The proteins of interest, in this case, Fn3 libraries, are expressed as fusion partners with the Aga2 protein.

These fusion proteins are secreted from the cell and become disulfide linked to the Aga1 protein, which is attached to the yeast cell wall (see Invitrogen, pYD1 Yeast Display product literature). The plasmid e.g, pYD1, prepared from an *E. coli* host by plasmid purification (Qiagen), is digested with the restriction enzymes, Bam HI and Not I, terminally dephosphorylated with calf intestinal alkaline phosphatase. Ligation of the pYD1 and CR products libraries, *E. coli* (DH5a) transformation and selection on LB-ampicillin (50 mg/ml) plates were performed using standard molecular biology protocols to amplify the libraries before electroporation into yeast cell hosts.

Methods for selecting expressed Fn3 library variants having substantially higher affinities for target ligands (e.g., TNF, VEGF, VEGF-R etc), relative to the reference wild type Fn3 domain, can be accomplished as follows.

Candidate test ligands (e.g., TNF, VEGF, VEGF-R etc), are fluorescently labeled (either directly or indirectly via a biotin-streptavidin linkage as described above). Those library clones that efficiently bind the labeled antigens are then enriched for by using FACS. This population of yeast cells is then re-grown and subjected to subsequent rounds of selection using increased levels of stringency to isolate a smaller subset of clones that recognize the target with higher specificity and affinity. The libraries are readily amenable to high-throughput formats, using, e.g., FITC labeled anti-Myc-tag FN3 binding domain molecules and FACS analysis for quick identification and confirmation. In addition, there are carboxyl terminal tags included which can be utilized to monitor expression levels and/or normalize binding affinity measurements.

To check for the display of the Aga2-Fn3 fusion protein, an aliquot of yeast cells ($8\times10^5$ cells in 40 µl) from the culture medium is centrifuged for 5 minutes at 2300 rpm. The supernatant is aspirated and the cell pellet is washed with 200 µl of ice cold PBS/BSA buffer (PBS/BSA 0.5% w/v). The cells are re-pelleted and supernatant removed before re-suspending in 100 µl of buffer containing the biotinylated TNFα (200 nM). The cells were left to bind the TNFα at 20° C. for 45 minutes after which they were washed twice with PBS/BSA buffer before the addition and incubation with streptavidin-FITC (2 mg/L) for 30 minutes on ice. Another round of washing in buffer was performed before final re-suspension volume of 400 μl in PBS/BSA. The cells were then analyzed on FACSscan (Becton Dickinson) using CellQuest software as per manufacturers directions.

To generate a library against TNFα, kinetic selections of the yeast displayed TNF-α fibronectin binding domain libraries involve initial labeling of cells with biotinylated TNF-α ligand followed by time dependent chase in the presence of large excess of un-biotinylated TNF-α ligand. Clones with slower dissociation kinetics can be identified by steptavidin-PE labeling after the chase period and sorted using a high speed FACS sorter. After Aga2-Fn3 induction, the cells are incubated with biotinylated TNFα at saturating concentrations (400 nM) for 3 hours at 25° C. under shaking. After washing the cells, a 40 hour cold chase using unlabelled TNFα (1 uM) at 25° C. The cells are then be washed twice with PBS/BSA buffer, labeled with Streptavidin PE (2 mg/ml) anti-HIS-FITC (25 nM) for 30 minutes on ice, washed and re-suspended and then analyzed on FACS ARIA sorter.

Ribosome Display:

Ribosome display utilizes cell free in vitro coupled transcription/translation machinery to produce protein libraries. The Fn3 library genes are inserted upstream to kappa light immunoglobulin gene that does not have a termination stop codon causing the ribosome to stall, but not release, when it reaches the end of the mRNA. Additionally, the kappa domain spacer serves to physically distance the Fn3 protein from the ribosome complex so that Fn3 binding domain has better accessibility to recognize its cognate ligand. The mRNA library is introduced into either S30 *E. coli* ribosome extract preparations (Roche) or rabbit reticulate lysate (Promega). In either case, the 5' end of the nascent mRNA can bind to ribosomes and undergo translation. During translation, the ligand-binding protein remains non-covalently attached to the ribosome along with its mRNA progenitor in a macromolecular complex.

The functional Fn3 proteins can then bind to a specific ligand that is either attached to magnetic beads or microtiter well surface. During the enrichment process, non-specific variants are washed away before the specific Fn3 binders are eluted. The bound mRNA is detected by RT-PCR using primers specific to the 5' Fn3 and 3' portion of the kappa gene respectively. The amplified double stranded cDNA is then cloned into an expression vector for sequence analysis and protein production.

For prokaryotic translation reactions, the reaction mix can contain 0.2 M potassium glutamate, 6.9 mM magnesium acetate, 90 mg/ml protein disulfide isomerase (Fluka), 50 mM Tris acetate (pH 7.5), 0.35 mM each amino acid, 2 mM ATP, 0.5 mM GTP, 1 mM cAMP, 30 mM acetyl phosphate, 0.5 mg/ml *E. coli* tRNA, 20 mg/ml folinic acid, 1.5% PEG 8000, 40 ml S30 *E. coli* extract and 10 mg mRNA in a total volume of 110 ml. Translation can be performed at 37° C. for 7 min, after which ribosome complexes can be stabilized by 5-fold dilution in ice-cold selection buffer (50 mM Tris acetate (pH 7.5), 150 mM NaCl, 50 mM magnesium acetate, 0.1% Tween 20, 2.5 mg/ml heparin).

Affinity Selection for Target Ligands.

Stabilized ribosome complexes can be incubated with biotinylated hapten (50 nM fluorescein-biotin (Sigma)) or antigen (100 nM IL-13 (Peprotech) biotinylated) as appropriate at 4° C. for 1-2 h, followed by capture on streptavidin-coated M280 magnetic beads (Dynal). Beads were then washed to remove non-specifically bound ribosome complexes. For prokaryotic selections, five washes in ice-cold selection buffer can be performed. For eukaryotic selections, three washes in PBS containing 0.1% BSA and 5 mM magnesium acetate were performed, followed by a single wash in PBS alone. Eukaryotic complexes can then be incubated with 10 U DNAse I in 40 mM Tris-HCl, 6 mM $MgCl_2$, 10 mMNaCl, 10 mM $CaCl_2$ for 25 min at 37° C., followed by three further washes with PBS, 5 mM magnesium acetate, 1% Tween 20.

Recovery of mRNA from Selected Ribosome Complexes

For analysis of mRNA recovery without a specific disruption step, ribosome complexes bound to magnetic beads can directly be processed into the reverse transcription reaction. For recovery of mRNA from prokaryotic selections by ribosome complex disruption, selected complexes can be incubated in EB20 [50 mM Tris acetate (pH 7.5), 150 mM NaCl, 20 mM EDTA, 10 mg/ml *Saccharomyces cerevisae* RNA] for 10 min at 4° C. To evaluate the efficiency of the 20 mM EDTA for recovery of mRNA from eukaryotic selections, ribosome complexes can be incubated in PBS20 (PBS, 20 mM EDTA, 10 mg/ml *S. cerevisae* RNA) for 10 min at 4° C. mRNA can be purified using a commercial kit (High Pure RNA Isolation Kit, Roche). For prokaryotic samples, the DNAse I digestion option of the kit was performed; however, this step is not required for eukaryotic samples, as DNAse I digestion was performed during post-selection washes. Reverse transcription can be performed on either 4 ml of purified RNA or 4 ml of immobilized, selected ribosome complexes (i.e. a bead suspension).

For prokaryotic samples, reactions contained 50 mM Tris-HCl (pH 8.3), 75 mM KCl, 3 mMMgCl2, 10 mMDTT, 1.25 primer, 0.5 mM PCR nucleotide mix (Amersham Pharmacia), 1 URNAsin (Promega) and 5 U SuperScript II (Invitrogen) and were performed by incubation at 50° C. for 30 min. For eukaryotic samples, reactions contained 50 mM Tris-HCl (pH 8.3), 50 mM KCl, 10 mM MgCl2, 0.5 mM spermine, 10 mM DTT, 1.25 mM RT primers, 0.5 mM PCR nucleotide mix, 1 U RNasin and 5 U AMV reverse transcriptase (Promega) and can be performed by incubation at 48° C. for 45 min.

PCR of Selection Outputs

End-point PCR can be performed to visualize amplification of the full-length construct. A 5 ml sample of each reverse transcription reaction can be amplified with 2.5 UTaq polymerase (Roche) in 20 mM Tris-HCl (pH 8.4), 50 mM KCl, 1 mM $MgCl_2$, 5% DMSO, containing 0.25 mM PCR nucleotide mix, 0.25 mM forward primer (T7B or T7KOZ for prokaryotic and or eukaryotic experiments, respectively) and 0.25 mM RT primer. Thermal cycling comprised 94° C. for 3 min, then 94° C. for 30 s, 50° C. for 30 s and 72° C. for 1.5 min for 30 cycles, with a final step at 72° C. for 5 min. PCR products were visualized by electrophoresis on an ethidium bromide stained agarose gels. The isolated PCR products can then be sub-cloned into a bacterial pBAD expression vector for soluble protein production.

Bacterial Expression and Production:

Competent *E. coli* host cells are prepared as per manufacturer's instructions (Invitrogen PBAD expression system). Briefly, 40 μl LMG 194 competent cells and 0.5 μl pBAD Fn3 constructs (approximately 1 μg DNA) can be incubated together on ice for 15 minutes after which, a one minute 42° C. heat shock was applied. The cells are then allowed to recover for 10 minutes at 37° C. in SOC media before plating onto LB-Amp plates and 37° C. growth overnight. Single colonies are picked the next day for small scale liquid cultures to initially determine optimal L-arabinose induction concentrations for Fn3 production. Replicates of each clone after reaching an OD600=0.5 can be tested induced with serial (1:10) titrations of L-arabinose (0.2% to 0.00002% final concentration) after overnight growth at room temperature. Test cultures (1 ml) can be collected, pelleted and 100 µl 1×BBS buffer (10 mM, 160 mM NaCl, 200 mM Boric acid, pH=8.0) added to resuspend the cells before the addition of 50 µl of lysozyme solution for 1 hour (37° C.). Cell supernatants from the lysozyme digestions can be collected after centrifugation, and $MgSO_4$ can be added to final concentration 40 mM. This solution can be applied to PBS pre-equilibrated Ni-NTA columns. His-tagged bound Fn3 samples are washed twice with PBS buffer upon which elution can be accomplished with the addition of 250 mM imidazole. Purity of the soluble Fn3 expression can be examined by SDS-PAGE.

EXEMPLIFICATION

Example 1: Methods for Bioinformatic-Guided Identification of Universal Fibronectin Bottom-Side Binding Domain Library Sequences In this example, universal AB, CD, and EF loop sequences for fibronectin binding domain library sequences are identified and selected using bioinformatics and the criteria of the invention. A generalized schematic of this process is presented in FIG. 1.

Briefly, the PFAM database was searched for a multiple sequence alignment containing only sequences belonging to the Fibronectin Type III family across all known species, including mammalian and human (Fn3, PFAM ID PF00041) in Stockholm 1.0 alignment format (pfam.janelia.org/family?entry=fn3#tabview=tab2).

This search returned an initial dataset of 15,520 protein sequences "base dataset". It is noted, however, that this set of sequences can increase in number as additional sequences are cloned and entered into the database. Within the starting 15,520 compiled sequences, the sequences will vary with respect to originating species, originating modules, loop lengths, and other qualities. Thus further refinement from the starting compiled sequences was conducted such that subset datasets share one or more of elected properties of interest, i.e., the presence of loops. Therefore, from the initial 15,520 downloaded sequences, redundant or duplicatively entered sequences, or incomplete sequences were removed and those containing the three loop sequences were identified, reducing the number of sequences to 12,452 "standard data set".

The next step involved the designation of the β-scaffold framework, loop lengths and loop amino acid sequences, followed by a frequency analysis of these candidate loop sequences. Therefore, determination of variability profiles entails collection and selection of aligned amino acid sequences that shares one or more defined properties of interest to create a dataset. A β-strand and loop positional classification system was designed using the positional numbering architecture of Fn3 domains as a reference point. β-strands were first identified based on the crystal structure of all Fn3 fibronectin-protein modules available from the RCSB Protein Data Bank (www.rcsb.org, H. M. Berman, J. Westbrook, Z. Feng, G. Gilliland, T. N. Bhat, H. Weissig, I. N. Shindyalov, P. E. Bourne; "The Protein Data Bank". Nucleic Acid Research, 28 pp. 235-242 (2000). An alignment of all the crystal structures identified regions of β-strands and potential regions of loops.

A Python script was written to extract data about the loops by alignment and binning according to loop length. The skilled artisan will appreciate that any methodology that aligns the loop regions and identified the amino acids at each position, can be used for this purpose. The analysis identified the following loop lengths for the bottom-side loops:

The AB loop contained 1 to 3 amino acids.
The CD loop contained 4 to 10 amino acids.
The EF loop contained 3 to 9 amino acids.
Acceptable sequences contained all 3 loops.
The Python script accepted 12,452 of the 15,520 downloaded sequences (80%)

The Python script analyzed each loop for the accepted sequences at each position for each length and categorized the loop length, the distribution of amino acids and the percentage abundance amino acid residues each position of the loops. One skilled in the art can appreciate that other gene sequences related to Fn1, Fn2 and other protein scaffold framework domains, such as SCALPs, nanobodies can also be searched in these databases and identified in similar manner.

The results of these analysis are shown in FIGS. 3-10. For example, the AB loop outer boundaries were determined to be between 1-3, with the majority of the sequences requiring a loop length of 3 (12, 265, FIGS. 3A and B). After setting the outer boundaries, the data was segregated into AB loop sizes and their amino acid frequency composition was determined (FIGS. 4A and B). The same principle was applied to the CD and EF loops as depicted in FIGS. 5-10 A-B.

Figure 3A:
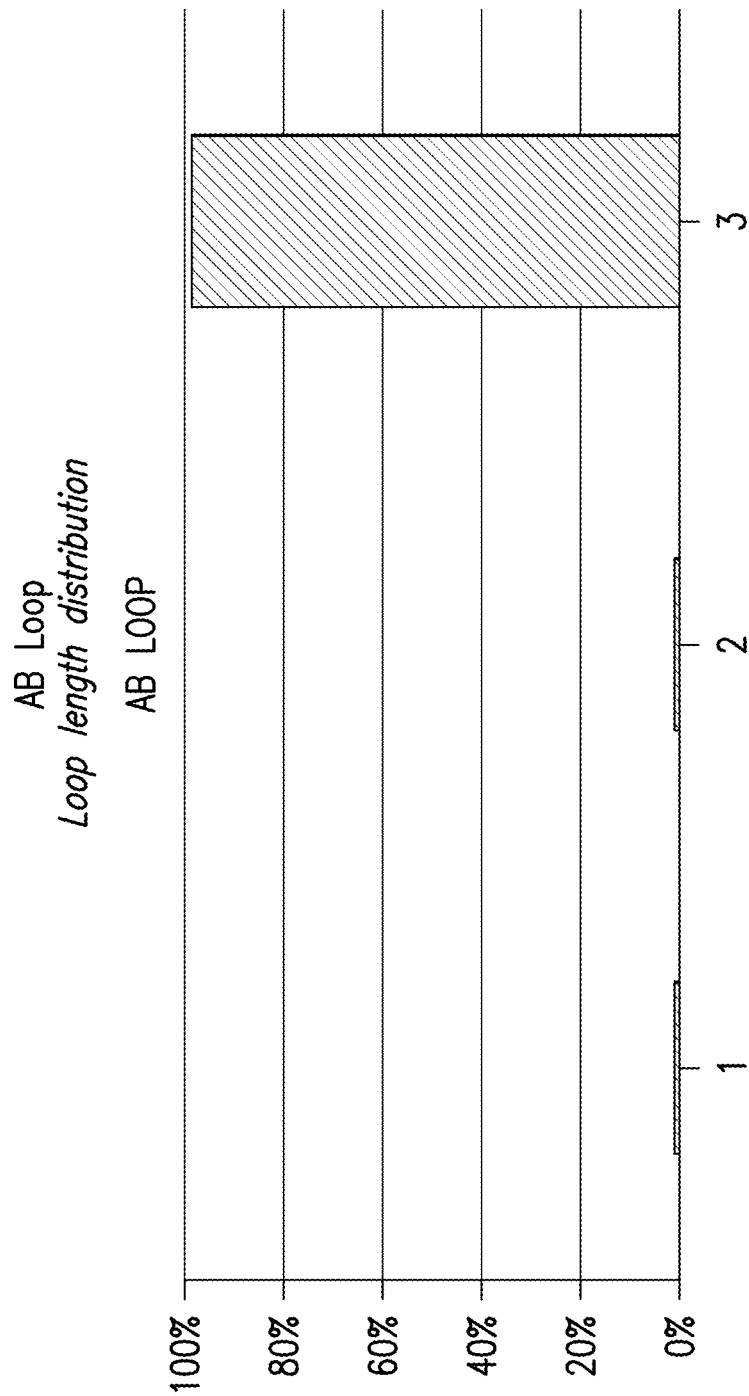
FIG. 3A is a bar graph showing AB loop length diversity derived from bioinformatics analysis of all Fn3 modules. AB loop length 3 is the single most predominant size seen in expressed Fn3 sequences.
Figure 4B:
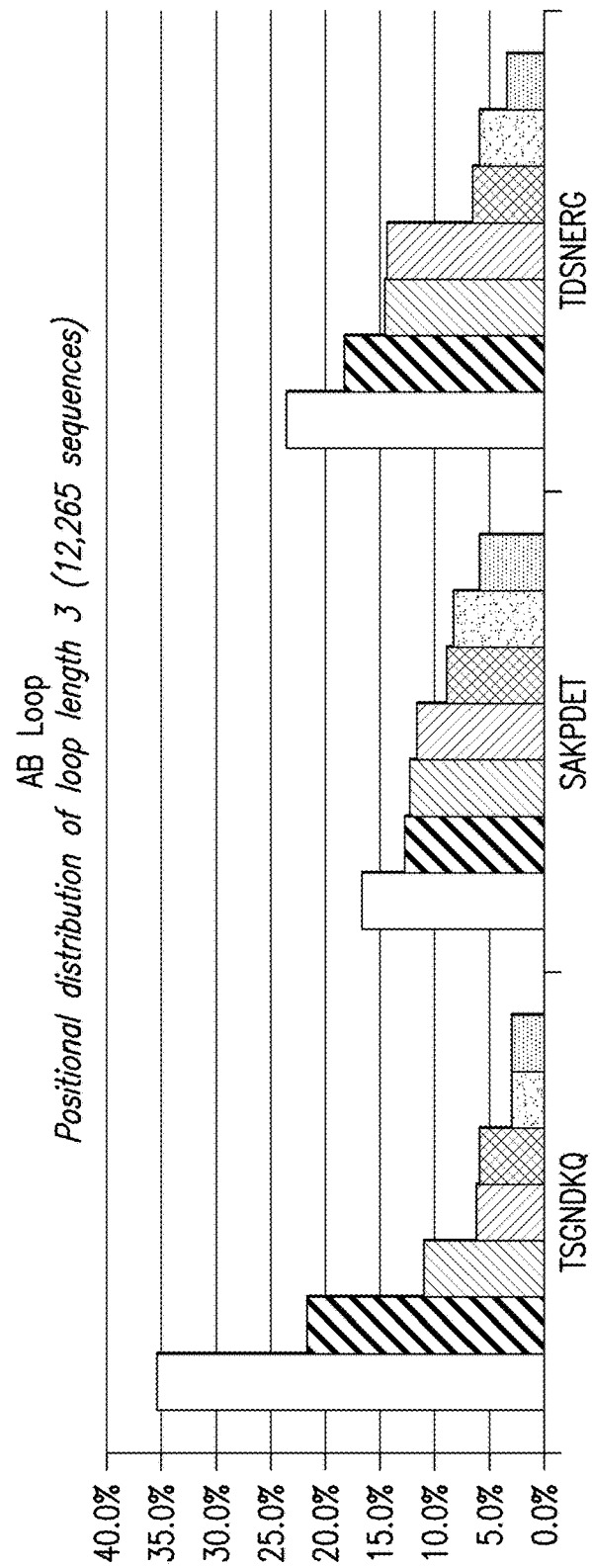
FIG. 4B is a bar graph showing sequence diversity of an exemplary loop region in the form of amino acid variability profile (frequency distribution) for the AB loop length size 3 (SEQ ID NOs. 2-4).
Figure 5A:
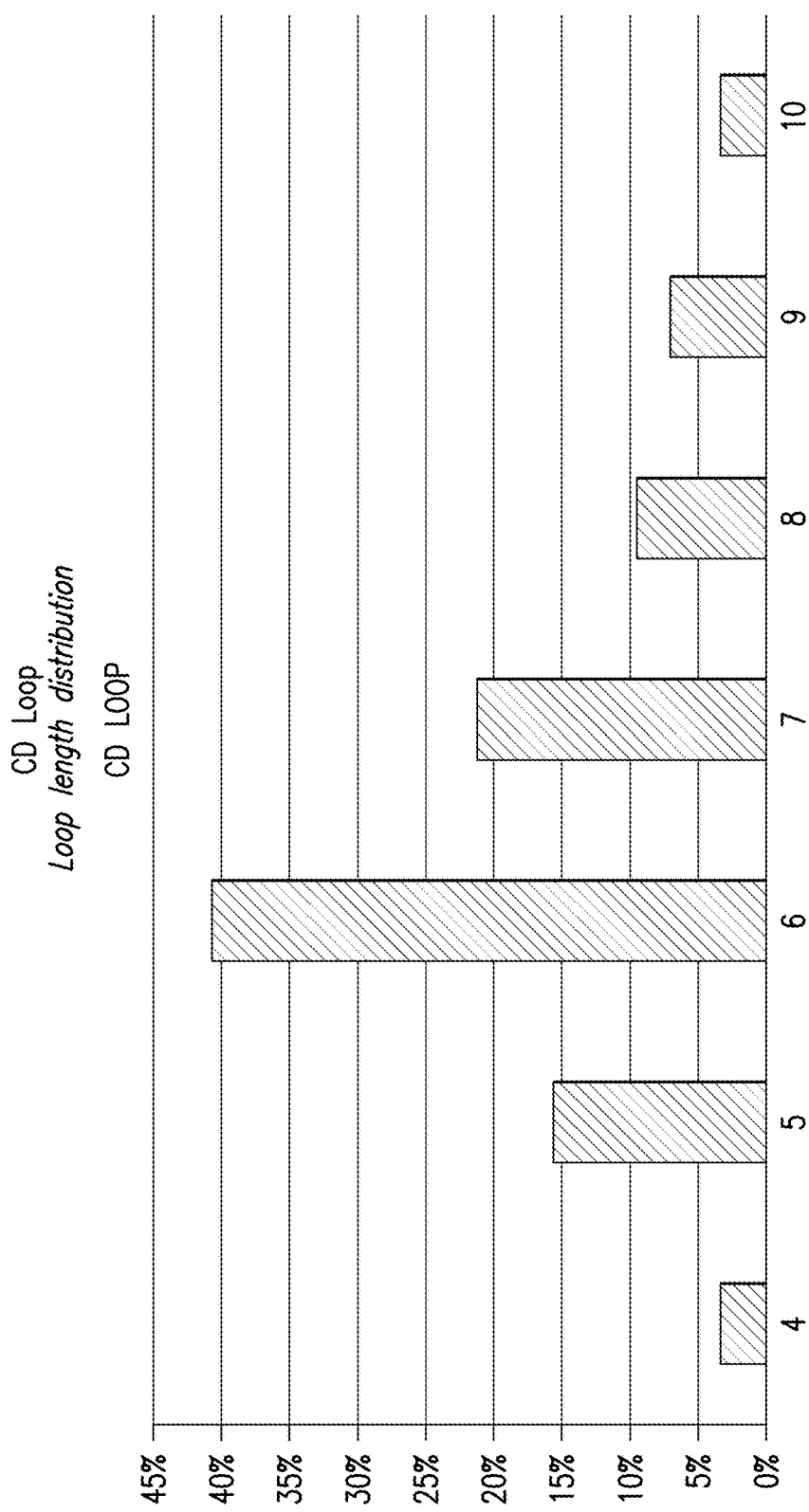
FIG. 5A is a bar graph showing CD loop length diversity derived from bioinformatics analysis of all Fn3 modules. CD loop lengths 5, 6 and 7 are the most predominant sizes seen in expressed Fn3 sequences.
Figure 8B:
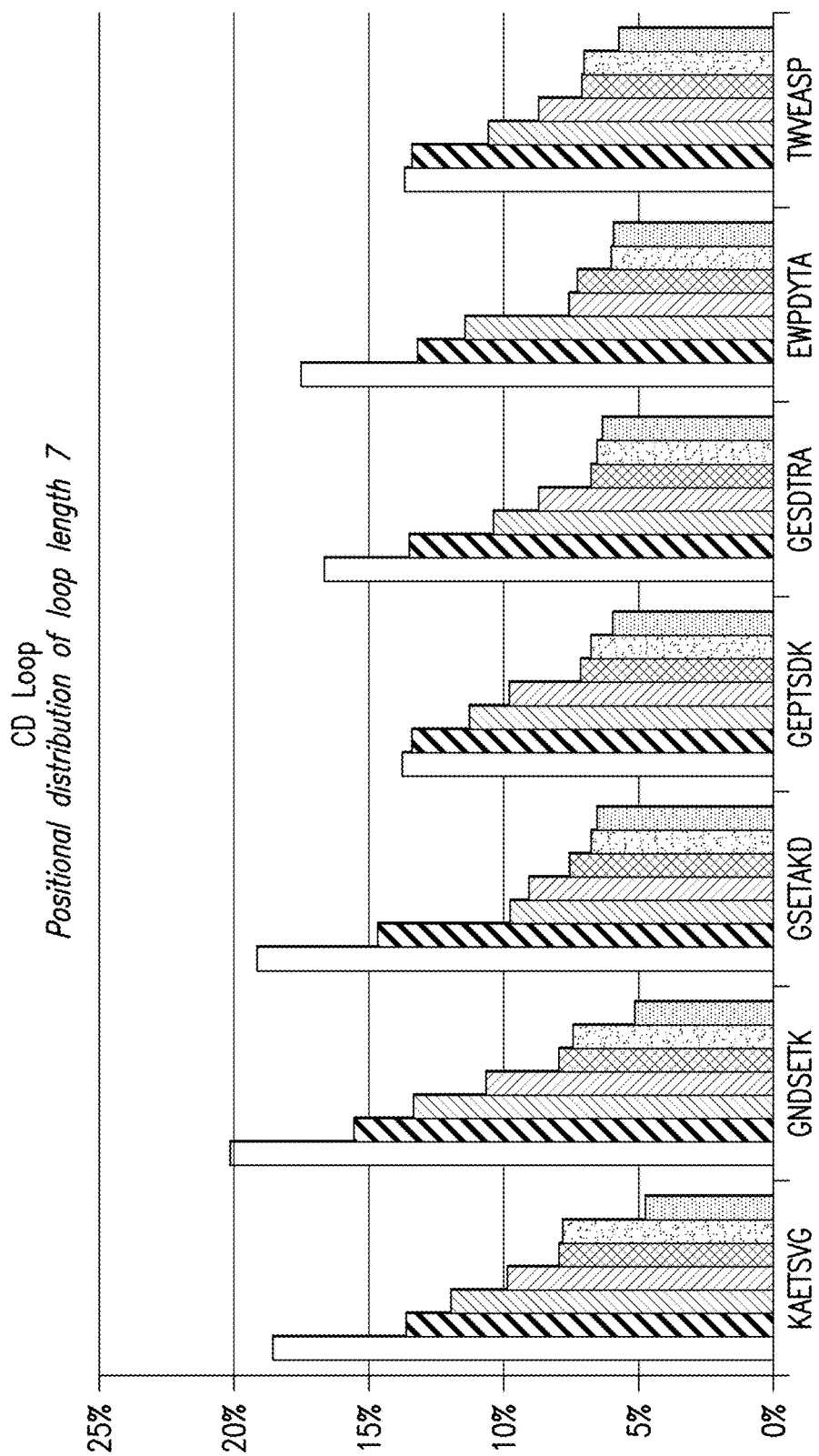
FIG. 8B is a bar graph showing sequence diversity of an exemplary loop region in the form of amino acid variability profile (frequency distribution) for the CD loop length size 7 (SEQ ID NOs. 16-22).

Based on these aligned β strand boundary definitions, the loops were found not be of one size, but to occur in differing lengths. The frequency distribution of the AB (FIG. 3AB), CD ((FIG. 5AB) and EF (FIG. 9AB) loop sizes were analyzed. The loop size classification and description follow the nomenclature of: Fn3 LOOP/LENGTH. For example AB/1-3 refers to Fn3 AB loop length of 1 to 3 amino acids, and AB/3 refers to Fn3 AB loop length of 3 amino acids. In the AB loop definition, the scaffold loop boundaries were originally set for 1-3 amino acid length, AB/1-3. The distribution of the 12,452 sequences identified loop length 3 as being the most predominant in the sequences, AB/3. Further examination of AB loop length of 3 was conducted (FIGS. 3-4 AB).

In the CD loop definition, the scaffold loop boundaries were originally set for 4-10 amino acid length, CD/4-10. The distribution of the 12,452 sequences identified loop lengths 5, 6, and 7 as being the most predominant in the sequences, CD/5, CD/6, and CD/7. Further examination of CD loop lengths of 5, 6, and 7 was conducted as this captures about 80% of the Fn3 molecules from the 12,452 sequence dataset (FIGS. 5-8AB).

Figure 9B:
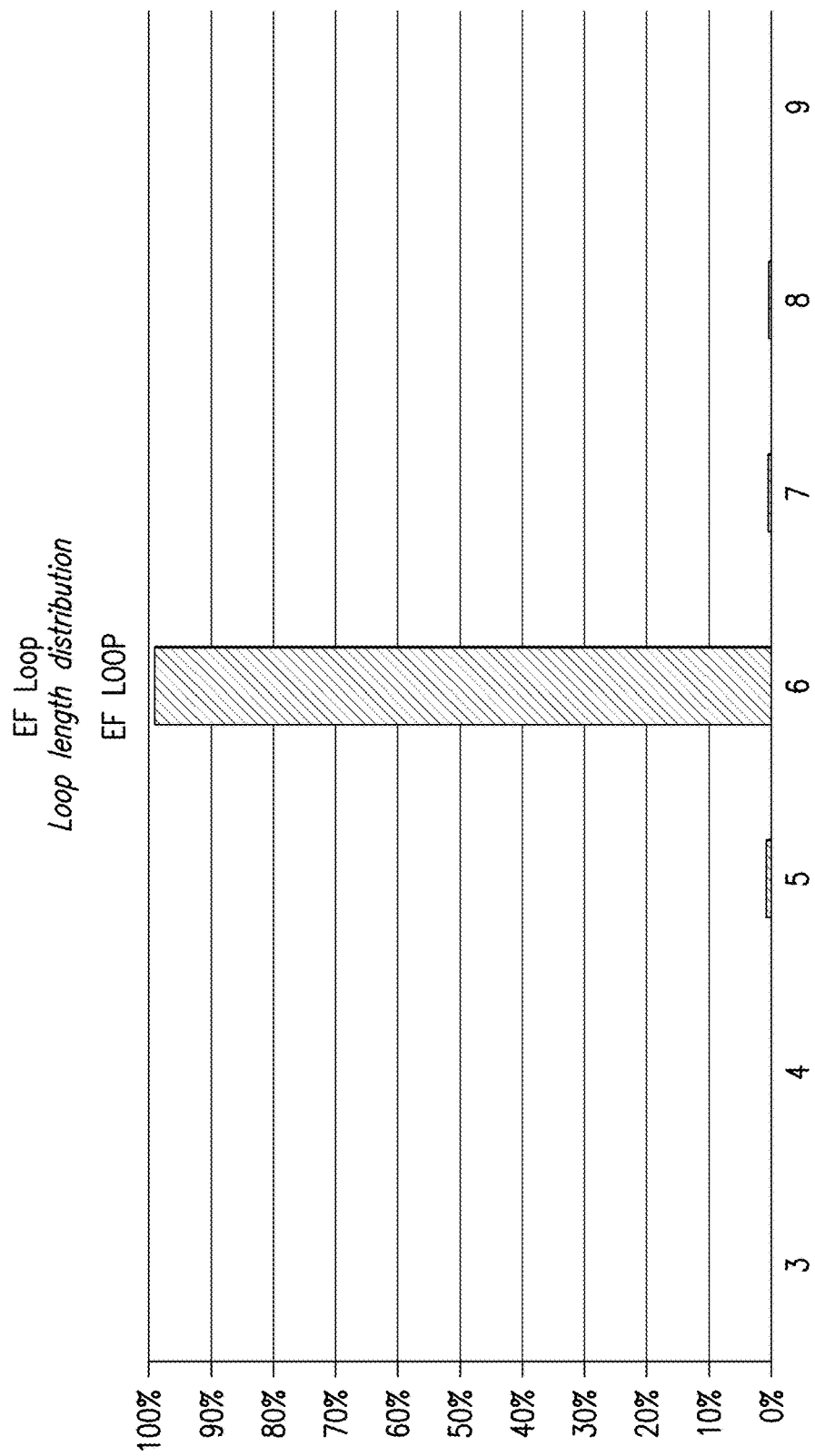
FIG. 9B is a bar graph showing EF loop length diversity derived from bioinformatics analysis of all Fn3 modules. EF loop length 6 is the single most predominant size seen in expressed Fn3 sequences.
Figure 10B:
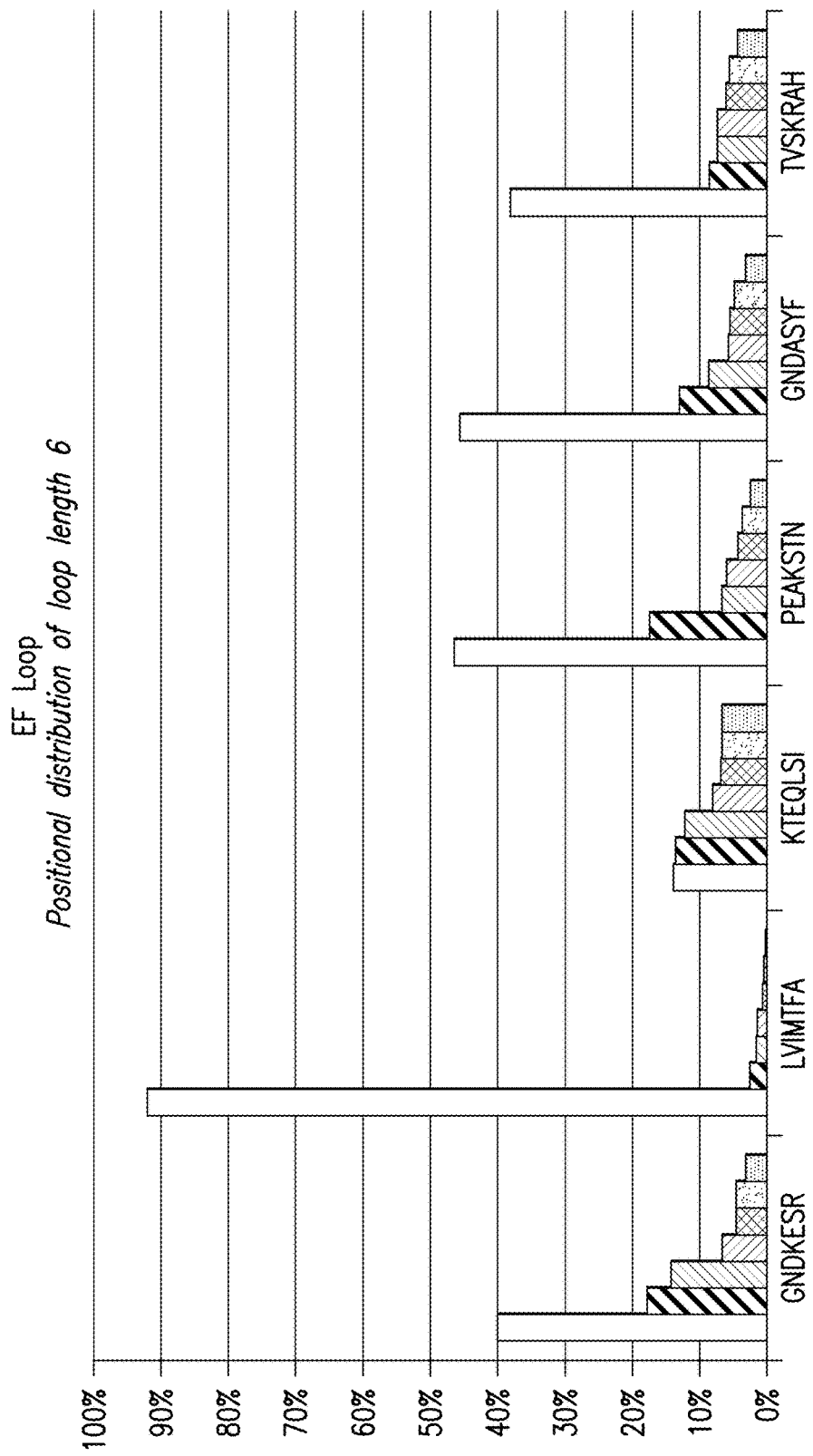
FIG. 10B is a bar graph showing sequence diversity of an exemplary loop region in the form of amino acid variability profile (frequency distribution) for the EF loop length size 6 (SEQ ID NOs. 23-28).

In the EF loop definition, the scaffold loop boundaries were originally set for 3-9 amino acid length, EF/3-9. The distribution of the 12,452 sequences identified loop lengths 6 was most predominant in the sequences, EF/6. Further examination of loop length 6 was conducted (FIGS. 9-10AB).

Example 2: Assessing Loop Variability Profiles Using Bioinformatics Through Filtering and Cluster Analysis of Gene Sequences The universal fibronectin binding domain libraries were designed by determining the variability profiles for the loops expressed in vivo. The variability profiles represent the cataloging of the different amino acids, and their respective rates of occurrence, present at a particular position in a dataset of aligned sequences. Size related families of loop sequences using the parameters set forth above within this starting "base dataset" can be identified and delineated. Comparative analysis of these multiple aligned loops provide variability profile information as to the existing and "tolerated" diversity for introducing amino acid changes that can lead to potential ligand binding. The designation of loops and their comprising amino acids can also be described for other scaffold like proteins using similar definitions.

The frequency distribution of the six loop sizes were generated to determine if there was preferred AB, CD and EF loop sizes for Fn3 sequences. For the AB loop a 3 amino acid loop size was the most predominant accounting for 98.50% of the AB loop population (FIG. 3AB). In this case, AB loop size 3 was chosen for further variability profile analysis, AB/3. (FIG. 4AB)

For the CD loop, CD loop sizes 5, 6, and 7 were the common sizes occurring at 15.56%, 40.59% and 21.00% of the CD loop population, respectively (FIG. 5AB). CD loop sizes 5, 6 and 7 were then chosen for the variability profile analysis, CD/5 (FIG. 6AB), CD/6 (FIG. 7AB), and CD7 (FIG. 8AB), respectively.

Frequency size analysis of the EF loop demonstrated that loop size 6 occurred in nearly 98.83% of the analyzed Fn3 sequences (FIG. 9AB). In this case, only EF loop size 6 was chosen for further variability profile analysis, EF/6 (FIG. 10AB).

TABLE 1

Lengths of Fn3 AB, CD, and EF loops analyzed along with the number of sequences indicate number

| Loop | Length | Number of Sequences | Percentage of Sequences |
|---|---|---|---|
| AB | 3 | 12,265 | 98.50 |
| CD | 5 | 1,937 | 15.56 |
| CD | 6 | 5,054 | 40.59 |
| CD | 7 | 2,615 | 21.00 |
| EF | 6 | 12,306 | 98.83 |

For each of the 5 selected loops (Table 1) a separate frequency analysis was executed to determine positional amino acid usage in the context of the selected loop. The output is visualized as frequency charts and the results are shown for the AB/3 loop in FIGS. 4AB; for CD/5 loop in FIGS. 6AB, CD/6 loop in FIGS. 7AB, CD/7 loop in FIGS. 8AB; and for the EF/6 loop in FIGS. 10AB.

Example 3: Identifying Fixed and Non-Fixed Loop Positions with Thresholds

In one embodiment, a natural-variant combinatorial library with a conserved or selected semi-conserved consensus amino acid is designed as follows.

Fn3 loop datasets are enumerated as above for amino acid variability and their relative frequencies at each aligned position (FIGS. 3-10). The above analysis identified positional preferences in all Fn3 module loops and are termed "variability profiles." For example, in AB loop size 3 (FIG. 4AB), a threonine (T) at position 1 is found at about 35%. There were no loop positions where a single amino acid accounted for more than 35% of the representative positional amino acids. There was a slight preference for serine (S) at position 2 over alanine (A); and for threonine (T) at position 3 over aspartic acid (D). In this case however, there were no predominant acids above a 40% threshold level to be considered "fixed" amino acids and all loop positions are considered "variable." For library construction, the most common amino acid in each loop position serves as the starting amino acid for first round mutagenesis. The AB/loop therefore has an all "variable" starting loop sequence of: X1 X2 X3, where X1 is any one of amino acids T, S, N, D, K, Q; X2 is any one of amino acids S, A, K, P, D, E, T; and X3 is any one of amino acids T, D, S, N, E, R, G.

For the 6 amino acid EF loop, a leucine (L) at position 2 within the loop is found at over 90% of all Fn3 loop positions demonstrating high degree of selective pressure for its presence. Thus, position 2 of the EF loop would be considered "conserved" for leucine (L) as it occurred above a predetermined 40% threshold level and was more than twice as common as the next most frequent amino acid at that position. This "fixed" residue is seen as the dominant amino acid with respect to the other amino acids that occur at that loop position. A "fixed" position may not be subject to mutagenic diversification in first round library building. Additionally, proline (P) at positions 4 within the loop occurs at frequency of >46% and can be also considered "fixed." By first determining these "fixed" positions and non-fixed positions (indicated by "X"), EF/6 would have a starting "fixed" sequence of: G1 L2 X3 P4 G5 X6, where X3 is any one of amino acids K, T, E, Q, L, S, and I, and X6 is any one of amino acids T, V, S, K, R, A, and H (SEQ ID NO. 29). In subsequent libraries G1 can also be altered to be any one of amino acids G, N, D, K, E, S, R; L2 can also be altered to be any one of amino acids L, V, I, M, T, F, A; P4 can also be altered to be any one of amino acids P, E, A, K, S, T, N; and G5 can also be altered to be any one of amino acids G, N, D, A, S, Y, F. The skilled artisan can appreciate that libraries can be generated using any combination of the amino acids in any positions of the EF/6 loop, as disclosed in FIGS. 10AB.

For the CD/5 loop, glycine (G) at position 3 within the loop is found at >49% and would be considered to be conserved and "fixed." There do not appear to be any predominant amino acids in positions 1, 2, 4 and 5 of the CD/5 loop, hence these would be considered to be "variable positions. Thus, a starting fixed sequence for the CD/5 loop would be X1, X2, G3, X4, X5, where X1 is any one of amino acids G, T, A, S, E, R, K; X2 is any one of amino acids D, G, N, S, E, Q, T; X4 is any one of amino acids Q, S, G, V, E, T, K; and X5 is any one of amino acids P, W, E, T, S, V, L. G3 can also be altered to be any one of amino acids G, S, K, D, A, T, N.

For the CD/6 loop, tryptophan (W) at position 6 within the loop is found at >59% and would be considered to be conserved and "fixed." There do not appear to be any predominant amino acids in positions 1, 2, 3, 4 and 5 of the CD/6 loop, hence these would be considered to be "variable positions. Thus, a starting fixed sequence for the CD/6 loop would be X1, X2, X3, X4, X5, W6, where X1 is any one of amino acids K, T, A, V, S, L, E; X2 is any one of amino acids G, D, S, N, E, T, K; X3 is any one of amino acids S, T, G, R, E, D, A; X4 is any one of amino acids G, E, D, T, K, N, S; and X5 is any one of amino acids E, R, T, K, D, A, Q. W6 can also be altered to be any one of amino acids W, E, P, T, A, Y, S.

For the CD/7 loop, there do not appear to be any predominant amino acids in positions 1, 2, 3, 4, 5, 6 or 7 within the loop, hence these would all be considered to be "variable positions. Thus, the starting loop sequence of X1 X2 X3 X4

X5 X6 X7 would be used, where X1 is any one of amino acids K, A, E, T, S, V, G; X2 is any one of amino acids G, N, D, S, E, T, K; X3 is any one of amino acids G, S, E, T, A, K, D; X4 is any one of amino acids G, E, P, T, S, D, K; X5 is any one of amino acids G, E, S, D, T, R, A; X6 is any one of amino acids E, W, P, D, Y, T, A; and X7 is any one of amino acids T, W, V, E, A, S, P.

The variability profile for each loop dataset then identifies the desired characteristics of a given loop position for further introduction of diversity representation. These above results demonstrate that the diversity of loop amino acids introduced into a library can be "fine-tuned" depending on the threshold level of frequency of occurrence. These "fixed" loop positions attempt to replicate some of the natural diversity to promote possible structural stabilization effects.

This "fixing" of positions also has the effect of "narrowing" the diversity of variable positions in starting loop sequences. However, there can be the occasion to perform the reverse, that is, to obtain larger more diverse libraries. In this case, the "widening" effect is accomplished by raising the threshold of frequency of occurrence used to designate "fixed" amino acids. In this way, the variability profile will capture fewer of the most conserved loop positions and classify them as "fixed" positions. The remaining loop positions would be part of the broader "variable" amino acids that can be diversified.

Each of the positions denoted as X will encode for the amino acids present in the related variability profile or for a subset of chemically equivalent ones. In fact in some cases two or more amino acids present at a certain position are chemically very similar. In such situations it is possible to include in the mutagenesis design only a subset of the amino acids and still preserve the natural chemistry characteristics of that position. This will both reduce the total number of mutants and give more flexibility for the optimization of the oligonucleotide synthesis.

Example 5: Identifying Fixed and Non-Fixed Loop Positions without Thresholds

In another embodiment it is possible to design natural-variation combinatorial diversity in each of the 5 selected loops (Table 1) without defining a variability threshold, i.e., where the selected threshold is 100%. In this embodiment each mutated loop is designed to contain amino acids that mimics its variability profile in terms of both variability and chemistry characteristics. At each specific loop position, oligonucleotide synthesis is optimized to contain a degenerate codon that would match/mimic the chemistry and the variability at that position. Positions having two or more amino acids in their variability profiles will be mutated regardless of the degree of variability of that position.

Example 6: Methods for Designing Loop Diversity for Fn3 Domain Libraries with Threshold Constraints In this example, methods for optimizing the loop diversity of an Fn3 binding domain library are presented. The choice of candidate frameworks, as previously noted, dictates both the loop sizes to be introduced and the initial amino acid sequence selection. The method is illustrated particularly for the EF/6 loop.

To design the EF/6 loop library for Fn3 based scaffolds, the variability profile considerations are as follows: As stated above, a "fixed" amino acid residue is determined to occur with a threshold frequency that is typically at least 40% (typically at least 50%) and is twice fold more frequent than the next most frequent amino acid for a given loop position. Upon inspection of the Fn3 EF/6 variability profile (FIG. 10AB), it can be seen that the leucine (L) at position 2 within the EF/6 loop was found to occur at >92%. The next most frequently occurring amino acids, was at frequency of less than 5% and did not register on the minimum threshold value. When a given residue, in this case leucine, is determined to occur at such a high frequency, it is highly conserved and thus represented in the libraries of the invention as "fixed," meaning that it will not be mutated in the first round library diversification.

Similarly, glycine (G) at position 1, proline (P) at position 4, and glycine (G) at position 5 within the EF/6 loop "highly conserved" as they occur at a frequency rate of 40%, >46%, and >45% respectively and are "fixed" in the first diversity library. In some cases, it can be that there are two semi-conserved amino acid residue at a given loop position. A "semi-fixed" position is one that has strong selective pressure with a first amino acid (e.g., >60%) and a lesser selective pressure for a second amino acid at the same position (e.g., >30%).

The reason for not creating diversity at all sites but using a "fixed" starting sequence is to restrict the initial diversity size of the library to facilitate efficient expression and display of all variants. These initially "fixed" positions indicate strong selective pressures for their preservation. However, they are still sites for further refinement during affinity maturation. In other words, the initial "fixed" positions can be later mutated. The overall goal in "fixing" positions in the first round library diversification is two fold: 1) to maximize the number of functional clones while by incorporating most of the preferred loop residues and 2) to minimize the total library size.

The term "variable" amino acid residue refers to amino acid residues determined to occur with a lower frequency (less than the high threshold value of 20%) for a given residue position. Upon inspection of the EF/6 variability profile for example (FIG. 10AB), it can be seen that variable position 3 within the loop has no single prevalent amino acid that occurs at higher than 40% frequency. For EF/6 position 3 each the EF/6 loop has many different amino acids occurring at a fairly low level frequency. Accordingly, the position 3 site is used for creation of initial loop sequence diversity by mutagenesis. All 20 amino acids and unnatural amino acids utilizing the amber codon can potentially be used for mutagenesis. (See e.g., US2009/0176654).

Example 7: Production of Libraries of Fibronectin Bottom-Side Binding Domains

In this example, the steps for making and assembling a universal fibronectin bottom side binding domain library using genetic engineering techniques are described.

Briefly, the fibronectin modules are cloned using standard molecular biology techniques. The oligonucleotides encoding the beta-strand scaffold framework and diversity loops of the variable regions can be assembled using polymerase chain reaction reactions. The full-length molecules are then amplified using flanking 5' and 3' primers containing restriction sites that facilitate cloning into the expression-display vector(s). The total diversity of the libraries generated depends on the number of framework sequences and number of positions in the loops chosen for mutagenesis.

Random clones from each library are then chosen for sequence verification and assessment of library quality with respect to desired mutational diversity, unintended point mutations, deletions, and insertions. This efficiency contrasts with random/stochastic mutagenesis strategies where uncontrolled introduction of various bases produces higher levels of undesired base change effects leading to low expression or fibronectin binding domains functionality due to unfavorable amino acid usage and inadvertent stop codons.

More specifically, $^{10}$Fn3 is used to design, isolate, and engineer universal fibronectin bottom-side binding domain libraries.

Library Construction

Wildtype $^{10}$Fn3 sequence as shown in SEQ ID NO: 1 was used as the basis to generate libraries of binders that utilize the top or bottom loops.

```
                                          (SEQ ID NO: 1)
VSDVPRDLEVVAATPTSLLISWDAPAVTVRYYRITYGETGGNSPVQEFT
VPGSKSTATISGLKPGVDYTITVYAVTGRGDSPASSKPISINYRTEI
```

Using the methods described in the above Examples, the wildtype $^{10}$Fn3 was mutagenized in the bottom loops AB, CD, EF to generate a library of fibronectin bottom-side binding domains (Bottom Library). The same method can be used to generate a library of fibronectin top-side binding domains using top loops BC, DE and FG (Top Library).

The DNA sequences corresponding to the Bottom Library is optimised for expression in *E. coli* at Geneart AG, Germany. The Bottom Library is assembled from synthetic degenerated oligonucleotides and genes corresponding to full length fragments and gel purified. Amplification is performed with terminal primers and subsequent ligation of the amplified library into cloning vector pCR-Script yield the starting libraries. The Bottom starting library is then screened to identify monospecific binders as described in Example 8 below.

Example 8: Screening of Monospecific Fibronectin-Based Binding Molecules

The present Example describes how to screen for fibronectin monospecific binders generated from the Bottom Library described in Example 7. The Bottom library is subcloned into a yeast display vector such as pYD1 (Invitrogen) using homologous recombination methods and transformed into a suitable strain such as EBY100 using standard molecular biology techniques.

Presentation and selection of fibronectin based binders against a target, e.g., hen egg lysozyme was conducted following essentially the protocol previously published by Lipovsek, D. et al, (*J Mol Biol*. 2007 May 11; 368(4):1024-41) with some minor modifications.

(i) Selection for Binding to Hen Egg White Lysozyme Using Magnetic Bead Sorting

For all selections, yeast cultures presenting the Bottom Library of $^{10}$Fn3-based molecules is induced for 18 h at 30° C. in galactose-containing medium (90% SG-CAA/10% SD-CAA, 50 µg/mL kanamycin, 100 U/mL penicillin G, 200 U/mL streptomycin). $10^9$ induced yeast cells of the Bottom Library is washed with 25 mL of ice-cold phosphate-buffered saline (PBS), pH 7.4, 2 mM ethylenediaminetetraacetic acid (EDTA), 0.5% bovine serum albumin (BSA) and then incubated in 5 mL of the same buffer containing 1 µM biotinylated hen egg white lysozyme (HEL-b, Sigma, St. Louis, Mo.) for 1 h at room temperature with gentle rotation. Following incubation, the sample is chilled on ice, washed with 25 mL of ice-cold PBS, pH 7.4, 2 mM EDTA, 0.5% BSA and resuspended in 2.5 mL of the same buffer. 100-µL aliquot of magnetic Streptavidin MicroBeads (Miltenyi Biotec, Auburn, Calif.) is added to the yeast and incubated on ice for 10 min. Ice-cold PBS, pH 7.4, 2 mM EDTA, 0.5% BSA is added to the sample to a total volume of 25 mL immediately before it is subjected to separation on an AutoMACS Cell Separator (Miltenyi Biotec), using the preset program for positive selection of rare cells (possels). Selected cells are collected in 6 mL SD-CAA, pH 4.5, 50 µg/mL kanamycin, 100 U/mL penicillin G, 200 U/mL streptomycin; quantified by serial dilution followed by plating on SD-CAA agar plates; and grown in 50 mL of the same medium for 2 days at 30° C.

(ii) Selection for Binding to Hen Egg White Lysozyme Using Fluorescence-Activated Cell Sorting Subsequent rounds of selection are performed by FACS, starting with $2 \times 10^6$ to $3 \times 10^6$ induced yeast cells. Cells are washed with 1 mL PBS, pH 7.4, 0.1% BSA, resuspended in 100 µL of the same buffer containing biotinylated hen egg white lysozyme, and incubated at room temperature with gentle rotation for 1 h.

After being washed with 1 mL of ice-cold PBS, pH 7.4, 0.1% BSA, the cells are labeled with antibodies and streptavidin. Mouse monoclonal FITC-conjugated anti-c-myc antibody (AbD Serotec) is used to label the yeast for surface display of c-myc-tagged antibody mimics, and PE-labeled streptavidin (Invitrogen) or anti-biotin antibody (Miltenyi) is used to label HEL-b associated with lysozyme-binding antibody mimics. The FACS sorts is performed on yeast cells labeled with FITC-conjugated mouse anti-c-myc antibody and PE-conjugated streptavidin (Invitrogen).

Double-labeled yeast cells are sorted on a Dako MoFlo high-speed cell sorter with a 488 nm laser, at 6000-10,000 cells/s. Gates are adjusted to collect the yeast cells with the highest 0.1-1% of HEL-b-associated signal (PE) and in the top half of expression-associated signal (FITC). Duplicate samples labeled with the same antibody and streptavidin reagents, but in the absence of HEL-b are used to avoid selecting the cells that bound detection reagents instead of lysozyme.

For all libraries, the first two FACS sorts are performed on yeast labeled with 1 µM HEL-b. Once a population of cells is observed that is labeled with PE in the presence but not in the absence of HEL-b, the concentration of HEL-b in the subsequent round is decreased by an order of magnitude. Selected cells are collected in 0.5 mL of SD-CAA, pH 4.5, 50 µg/mL kanamycin, 100 U/mL penicillin G, and 200 U/mL streptomycin. The collected cells are grown to saturation in 5 mL of the same medium, with shaking, for 2 days at 30° C., before being induced and labeled for the next round of sorting.

After several rounds of FACS sorting the final enriched population is plated out on SDCAA plates and incubated at 30° C. for 2 days. Individual colonies are picked using a Genetix Clonepix and re-arrayed into 96 well plates containing SD-CAA medium. After incubation for 24 hours the cells are collected by centrifugation and re-suspended in SD-GAA medium for induction of surface expressed unique Fn3 molecules. Positive clones are identified by standard ELISA. Plasmid DNA corresponding to the unique Fn3 positive clones is purified and sequenced to identify monospecific binders.

Once monospecific binders are identified and selected from the Bottom Library, they can be used to generate therapeutic molecules. In particular, the monospecific binders generated from the Bottom Library can be used to generate novel therapeutic binding molecules against a target of interest. Various monospecific binders from the Bottom Library can be combined with linkers to produce a Fn3 binding molecule that is capable of binding to one or more regions of a single target (e.g., TNF). Alternately, a Fn3 binding molecule comprising binders from the Bottom Library can also be designed to bind to one or more regions of multiple targets (e.g., one or more regions of HSA and TNF).

In addition, the monospecific binders generated from Bottom Library can be combined with the Top Library using standard molecular biology technique to generate bispecific and multispecific binders.

Example 9: Generation of Bifunctional Fibronectin-Based Binding Molecules

Computer modeling of the randomized regions onto the x-ray structure of human Fn3 shows that by combining monospecific binders of each of the libraries A and B, one can create a bispecific fibronectin binding molecules. These binding molecules can be engineered such that they recognizes different regions on the same target molecule, or that the different binding sites of the bispecific or multispecific fibronectin molecule can bind to different regions on two or more different targets.

For example, a suitable sequence corresponding to the Bottom Loops (obtained by screening the Bottom Library) and a suitable sequence corresponding to the Top Loops (obtained by screening the Top Library) can be combined into one single molecule, Binder C which uses both the Bottom and Top Loops to bind, thus generating a bispecific molecule.

The DNA corresponding to the combined amino acid sequence of Binder C is then synthesized and optimised for expression in *E. coli* at Geneart AG, Germany. Cloning into *E. coli* and subsequent purification follows standard protocols as outlined in chapter 4 (Methods of manufacture).

Alternatively, a bifunctional Fn3-based binding molecule an be generated by linking two or more monospecific Fn3-based binding molecules.

EQUIVALENTS

Those skilled in the art will recognize or be able to ascertain, using no more than routine experimentation, many equivalents of the specific embodiments of the invention described herein. Such equivalents are intended to be encompassed by the following claims.

The contents of any patents, patent applications, and references cited throughout this specification are hereby incorporated by reference in their entireties.

The invention claimed is:

1. A natural-variant combinatorial library of fibronectin Type 3 (Fn3) domain polypeptides useful in screening for the presence of one or more polypeptides having a selected binding or enzymatic activity, said polypeptides comprising:

(a) regions A, B, C, D, E, F, and G having wild-type amino acid sequences of a selected native fibronectin Type 3 polypeptide, and (b) loop regions AB, CD, and EF having selected lengths, wherein the AB loop length is set at 3 amino acids (AB/3), where at least one selected loop region of a selected length contains a library of natural-variant combinatorial sequences expressed by a library of coding sequences that encode, at each loop position, a conserved or selected semi-conserved consensus amino acid and, if the consensus amino acid has a frequency of occurrence equal to or less than a selected threshold frequency of at least 50%, other natural variant amino acids, including semi-conserved amino acids and variable amino acids whose occurrence rate is above a selected minimum threshold occurrence at that position, or their chemical equivalents.

2. The library of claim 1, which has a library of natural-variant combinatorial sequences at a combination of loops and loop lengths selected from loops
   I. CD, where the CD loop is selected from one of CD/4-10, CD/5, CD/6, and CD/7
   II. EF, where the EF loop is selected from one of EF/3-9, EF/6, and
   III. CD and EF, where the CD loop is selected from one of CD/4-10, CD/5, CD/6, and CD/7, and the EF loop is selected from one of EF/3-9 or EF/6.

3. The library of claim 2, which has a given threshold is 100%, unless the loop amino acid position contains only one dominant and one variant amino, and the dominant and variant amino have side chains with similar physiochemical properties, in which case the given threshold is 90%.

4. The library of claim 2, wherein said polypeptides have the wild-type amino acid sequences in beta-strand regions A, B, C, D, E, F, and G of the 10th fibronectin Type III module of human fibronectin.

5. The library of claim 2, wherein said polypeptides have the wild: type amino acid sequences in regions A, B, C, D, E, F, and G of the 14th fibronectin Type III module of human fibronectin.

6. The library of claim 2, wherein the CD loop length is 5.

7. The library of claim 2, wherein the CD loop length is 6.

8. The library of claim 2, wherein the CD loop length is 7.

9. The library of claim 2, wherein the EF loop length is 6.

10. The library of claim 2, wherein the polypeptides are encoded by an expression library selected from the group consisting of a ribosome display library, a polysome display library, a phage display library, a bacterial expression library, and a yeast display library.

11. A method of identifying a polypeptide having a desired binding affinity with respect to a selected antigen, comprising
    reacting the natural-variant combinatorial library of Fn3 polypeptides of claim 2 with the selected antigen, and
    screening the Fn3 polypeptides to select those having a desired binding affinity with respect to the selected antigen.

12. The method of claim 11, wherein the method further comprises the step of identifying the polynucleotide that encodes the selected fibronectin binding domain.

* * * * *

SEQUENCE LISTING

```
<160> NUMBER OF SEQ ID NOS: 34

<210> SEQ ID NO 1
<211> LENGTH: 96
<212> TYPE: PRT
<213> ORGANISM: Homo sapiens

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 2

Thr Ser Gly Asn Asp Lys Gln
1               5

<210> SEQ ID NO 3
<211> LENGTH: 7
<212> TYPE: PRT
<213> ORGANISM: Artificial Sequence
```

```
<220> FEATURE:
<223> OTHER INFORMATION: Synthetic Peptide

<400> SEQUENCE: 3

Ser Ala Lys Pro Asp Glu Thr
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 4

Thr Asp Ser Asn Glu Arg Gly
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 5

Gly Thr Ala Ser Glu Arg Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 6

Asp Gly Asn Ser Glu Gln Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 7

Gly Ser Lys Asp Ala Thr Asn
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 8

Gln Ser Gly Val Glu Thr Lys
1               5

<210> SEQ ID NO 9
<211> LENGTH: 7
<212> TYPE: PRT
<213> ORGANISM: Artificial Sequence
<220> FEATURE:
```

<223> OTHER INFORMATION: Synthetic Peptide

<400> SEQUENCE: 9

Pro Trp Glu Thr Ser Val Leu
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 10

Lys Thr Ala Val Ser Leu Glu
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 11

Gly Asp Ser Asn Glu Thr Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 12

Ser Thr Gly Arg Glu Asp Ala
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 13

Gly Glu Asp Thr Lys Asn Ser
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 14

Glu Arg Thr Lys Asp Ala Gln
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 15

Trp Glu Pro Thr Ala Tyr Ser
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 16

Lys Ala Glu Thr Ser Val Gly
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 17

Gly Asn Asp Ser Glu Thr Lys
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 18

Gly Ser Glu Thr Ala Lys Asp
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 19

Gly Glu Pro Thr Ser Asp Lys
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 20

Gly Glu Ser Asp Thr Arg Ala
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic Peptide

```
<400> SEQUENCE: 21

Glu Trp Pro Asp Tyr Thr Ala
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 22

Thr Trp Val Glu Ala Ser Pro
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 23

Gly Asn Asp Lys Glu Ser Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 24

Leu Val Ile Met Thr Phe Ala
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 25

Lys Thr Glu Gln Leu Ser Ile
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 26

Pro Glu Ala Lys Ser Thr Asn
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 27
```

```
Gly Asn Asp Ala Ser Tyr Phe
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 28

Thr Val Ser Lys Arg Ala His
1               5

<210> SEQ ID NO 29
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X can be any one of amino acids T, S, N, D, K,
      Q
<220> FEATURE:
<221> NAME/KEY: MISC_FEATURE
<222> LOCATION: (2)..(2)
<223> OTHER INFORMATION: X can be any one of amino acids S, A, K, P, D,
      E, T
<220> FEATURE:
<221> NAME/KEY: MISC_FEATURE
<222> LOCATION: (3)..(3)
<223> OTHER INFORMATION: X can be any one of amino acids T, D, S, N, E,
      R, G

<400> SEQUENCE: 29

Xaa Xaa Xaa
1

<210> SEQ ID NO 30
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: In subsequent libraries G can be any one of
      amino acids G, N, D, K, E, S, R
<220> FEATURE:
<221> NAME/KEY: MISC_FEATURE
<222> LOCATION: (2)..(2)
<223> OTHER INFORMATION: In subsequent libraries L can be any one of
      amino acids L, V, I, M, T, F, A
<220> FEATURE:
<221> NAME/KEY: MISC_FEATURE
<222> LOCATION: (3)..(3)
<223> OTHER INFORMATION: X can be any one of amino acids K, T, E, Q, L,
      S, I
<220> FEATURE:
<221> NAME/KEY: MISC_FEATURE
<222> LOCATION: (4)..(4)
<223> OTHER INFORMATION: In subsequent libraries, P can be any one of
      amino acids P, E, A, K, S, T, N
<220> FEATURE:
<221> NAME/KEY: MISC_FEATURE
<222> LOCATION: (5)..(5)
<223> OTHER INFORMATION: In subsequent libraries, G can be any one of
      amino acids G, N, D, A, S, Y, F
<220> FEATURE:
<221> NAME/KEY: MISC_FEATURE
```

```
<222> LOCATION: (6)..(6)
<223> OTHER INFORMATION: X can be any one of amino acids T, V, S, K, R,
      A, H

<400> SEQUENCE: 30

Gly Leu Xaa Pro Gly Xaa
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is any one of amino acids G, T, A, S, E, R, K
<220> FEATURE:
<221> NAME/KEY: MISC_FEATURE
<222> LOCATION: (2)..(2)
<223> OTHER INFORMATION: X is any one of amino acids D, G, N, S, E, Q, T
<220> FEATURE:
<221> NAME/KEY: MISC_FEATURE
<222> LOCATION: (3)..(3)
<223> OTHER INFORMATION: G can be altered to be any one of amino acids
      G, S, K, D, A, T, N
<220> FEATURE:
<221> NAME/KEY: MISC_FEATURE
<222> LOCATION: (4)..(4)
<223> OTHER INFORMATION: X can be be any one of amino acids Q, S, G, V,
      E, T, K
<220> FEATURE:
<221> NAME/KEY: MISC_FEATURE
<222> LOCATION: (5)..(5)
<223> OTHER INFORMATION: X can be be any one of amino acids P, W, E, T,
      S, V, L

<400> SEQUENCE: 31

Xaa Xaa Gly Xaa Xaa
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X can be any one of amino acids K, T, A, V, S,
      L, E
<220> FEATURE:
<221> NAME/KEY: MISC_FEATURE
<222> LOCATION: (2)..(2)
<223> OTHER INFORMATION: X can be any one of amino acids G, D, S, N, E,
      T, K
<220> FEATURE:
<221> NAME/KEY: MISC_FEATURE
<222> LOCATION: (3)..(3)
<223> OTHER INFORMATION: X can be any one of amino acids S, T, G, R, E,
      D, A
<220> FEATURE:
<221> NAME/KEY: MISC_FEATURE
<222> LOCATION: (4)..(4)
<223> OTHER INFORMATION: X can be any one of amino acids G, E, D, T, K,
      N, S
<220> FEATURE:
<221> NAME/KEY: MISC_FEATURE
<222> LOCATION: (5)..(5)
<223> OTHER INFORMATION: X can be any one of amino acids E, R, T, K, D,
      A, Q
<220> FEATURE:
<221> NAME/KEY: MISC_FEATURE
```

```
<222> LOCATION: (6)..(6)
<223> OTHER INFORMATION: W can be altered to be ny one of amino acids W,
      E, P, T, A, Y, S

<400> SEQUENCE: 32

Xaa Xaa Xaa Xaa Xaa Trp
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X can be any one of amino acids K, A, E, T, S,
      V, G
<220> FEATURE:
<221> NAME/KEY: MISC_FEATURE
<222> LOCATION: (2)..(2)
<223> OTHER INFORMATION: X can be any one of amino acids G, N, D, S, E,
      T, K
<220> FEATURE:
<221> NAME/KEY: MISC_FEATURE
<222> LOCATION: (3)..(3)
<223> OTHER INFORMATION: X can be any one of amino acids G, S, E, T, A,
      K, D
<220> FEATURE:
<221> NAME/KEY: MISC_FEATURE
<222> LOCATION: (4)..(4)
<223> OTHER INFORMATION: X can be any one of amino acids G, E, P, T, S,
      D, K
<220> FEATURE:
<221> NAME/KEY: MISC_FEATURE
<222> LOCATION: (5)..(5)
<223> OTHER INFORMATION: X can be any one of amino acids G, E, S, D, T,
      R, A
<220> FEATURE:
<221> NAME/KEY: MISC_FEATURE
<222> LOCATION: (6)..(6)
<223> OTHER INFORMATION: X can be any one of amino acids E, W, P, D, Y,
      T, A
<220> FEATURE:
<221> NAME/KEY: MISC_FEATURE
<222> LOCATION: (7)..(7)
<223> OTHER INFORMATION: X can be any one of amino acids T, W, V, E, A,
      S, P

<400> SEQUENCE: 33

Xaa Xaa Xaa Xaa Xaa Xaa Xaa
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 34

Gly Asp Gly Gln Pro
1               5
```